United States Patent
Sun et al.

(10) Patent No.: US 11,925,611 B2
(45) Date of Patent: Mar. 12, 2024

(54) USE OF ZT-1A AND ANALOGS THEREOF TO PREVENT AND/OR TREAT NEURODEGENERATIVE AND NEUROCOGNITIVE DISORDERS

(71) Applicants: United States Government as Represented by the Department of Veterans Affairs, Washington, DC (US); University of Pittsburgh—of the Commonwealth of Higher Education, Pittsburgh, PA (US)

(72) Inventors: Dandan Sun, Pittsburgh, PA (US); Mohammad Iqbal Hossain Bhuiyan, Pittsburgh, PA (US)

(73) Assignees: United States Government as represented by the Department of Veterans Affairs, Washington, DC (US); University of Pittsburgh - of the Commonwealth of Higher Education, Pittsburgh, PA (US)

( * ) Notice: Subject to any disclaimer, the term of this patent is extended or adjusted under 35 U.S.C. 154(b) by 0 days.

(21) Appl. No.: 17/704,789

(22) Filed: Mar. 25, 2022

(65) Prior Publication Data
US 2022/0313632 A1 Oct. 6, 2022

Related U.S. Application Data

(60) Provisional application No. 63/166,847, filed on Mar. 26, 2021.

(51) Int. Cl.
*A61K 31/167* (2006.01)
*A61P 25/28* (2006.01)

(52) U.S. Cl.
CPC ............ *A61K 31/167* (2013.01); *A61P 25/28* (2018.01)

(58) Field of Classification Search
CPC .............................. A61P 25/28; A61K 31/167
See application file for complete search history.

(56) References Cited

U.S. PATENT DOCUMENTS

| | | | |
|---|---|---|---|
| 2011/0251239 A1 | 10/2011 | Moline et al. | |
| 2017/0326160 A1 | 11/2017 | Delavenne et al. | |
| 2020/0085817 A1 | 3/2020 | Jaenisch et al. | |
| 2020/0102266 A1 | 4/2020 | Sun et al. | |

FOREIGN PATENT DOCUMENTS

| | | |
|---|---|---|
| AU | 2019351731 | 9/2019 |
| CA | 3115075 | 9/2019 |
| CN | 2019800656115 | 9/2019 |
| EP | 19868524 | 9/2019 |
| WO | WO 2018/173069 A1 | 9/2018 |
| WO | PCT/US2019/053887 | 9/2019 |
| WO | WO 2020/072386 A1 | 4/2020 |
| WO | WO 2020/084105 A2 | 4/2020 |
| WO | PCT/US2022/021952 | 3/2022 |
| WO | WO 2022/204519 | 9/2022 |
| ZA | 2021/02261 | 9/2019 |

OTHER PUBLICATIONS

Modulation of brain cation-Cl-cotransport via the SPAK kinase inhibitor ZT-1a Zhang et al. Published online Jan. 7, 2020. doi: 10.1038/s41467-019-13851-6 (Year: 2020).*
Is Stroke a Neurodegenerative Condition? A Critical Review of Secondary Neurodegeneration and Amyloid-beta Accumulation after Stroke Ong et al. AIMS Medical Science vol. 4, Issue 1, 1-16 (Year: 2017).*
Modulation of brain cation-Cl-cotransport via the SPAK kinase inhibitor ZT-1a Zhang et al. Nature Communications, (2020) 11:78 (Year: 2020).*
U.S. Appl. No. 62/740,336, filed Oct. 2, 2019.
U.S. Appl. No. 16/588,751, filed Sep. 30, 2019.
U.S. Appl. No. 17/177,056, filed Feb. 16, 2021.
U.S. Appl. No. 63/166,847, filed Mar. 26, 2021.
Ellsworth et al. Document No. 131: 295129, retrieved from STN; 1999.
Gojon-Zorrilla et al. Document No. 164: 159252, retrieved from STN; entered in STN on Jan. 8, 2016.
Jakobsen et al. Document No. 150:555798, retrieved from STN; entered in STN on May 22, 2009.
Janssen et al. Document No. 86: 55186, retrieved from STN; entered in STN on May 12, 1984.
Kikuchi et al. (2015) "Discovery of Novel SPAK Inhibitors That Block WNK Kinase Signaling to Cation Chloride Transporters," *Basic Research* 26: 1525-1536.
Pubchem CID 97289639, Create date Dec. 11, 2015, Accessed Jan. 20, 2020, p. 2.
Zhang et al. (2020) "Modulation of brain cation-Cl-cotransport via the SPAK kinase inhibitor ZT-1a," *Nature Communications* 11: 1-17.

* cited by examiner

*Primary Examiner* — Jeffrey S Lundgren
*Assistant Examiner* — Eric Tran
(74) *Attorney, Agent, or Firm* — Ballard Spahr LLP

(57) ABSTRACT

The present disclosure is concerned with substituted N-(5-chloro-4-((4-chlorophenyl)(cyano)methyl)-2-methylphenyl) benzamide compounds, and methods of treating and/or preventing neurodegenerative or neurocognitive disorders including, but not limited to, Alzheimer's disease, cerebral autosomal dominant arteriopathy with sub-cortical infarcts and leukoencephalopathy (CADASIL), Parkinson's disease, Huntington's disease, amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia, Lewy body disease, and dementia (e.g., vascular dementia, Lewy body dementia, frontotemporal dementia, mixed dementia, dementia induced by Alzheimer's disease or Parkinson's disease). This abstract is intended as a scanning tool for purposes of searching in the particular art and is not intended to be limiting of the present invention.

18 Claims, 20 Drawing Sheets

USE OF ZT-1A AND ANALOGS THEREOF TO PREVENT AND/OR TREAT NEURODEGENERATIVE AND NEUROCOGNITIVE DISORDERS

CROSS-REFERENCE TO RELATED APPLICATIONS

This Application claims the benefit of U.S. Application No. 63/166,847, filed on Mar. 26, 2021, the contents of which are incorporated herein by reference in their entirety.

STATEMENT REGARDING FEDERALLY SPONSORED RESEARCH

This invention was made with government support under grant number I01BX002891 awarded by the Department of Veterans Affairs. The government has certain rights in the invention.

BACKGROUND

Stroke is one of the most significant risk factors that leads to dementia. Vascular dementia is generally considered the second most common subtype of dementia, after dementia induced by Alzheimer's disease, accounting for roughly 15% to 20% of dementia cases in North America and Europe. The most common feature of vascular dementia is diffuse white matter lesions, detected as white matter hyperintensities on T2-weighted MRI. The longitudinal studies demonstrate that increasing white matter injury volume predicts cognitive decline, mild cognitive impairment, incident dementia, and stroke. To date, the hallmark of white matter injury represents increased water content in white matter tracks and is associated with axonal damage and white matter edema. The underlying molecular and cellular mechanisms of vascular dementia, however, remain unknown. Thus, despite the widespread prevalence, there are no known therapies for treating dementia. Therefore, there remains a need for compounds for treating and preventing dementia and other neurocognitive disorders, as well as neurodegenerative disorders that can result in dementia, and methods of making and using same. These needs and others are met by the present invention.

SUMMARY

In accordance with the purpose(s) of the invention, as embodied and broadly described herein, the invention, in one aspect, relates to substituted N-(5-chloro-4-((4-chlorophenyl)(cyano)methyl)-2-methylphenyl)benzamide compounds useful in the treatment and/or prevention of neurodegenerative or neurocognitive disorders including, but not limited to, Alzheimer's disease, cerebral autosomal dominant arteriopathy with sub-cortical infarcts and leukoencephalopathy (CADASIL), Parkinson's disease, Huntington's disease, amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia, Lewy body disease, and dementia (e.g., vascular dementia, Lewy body dementia, frontotemporal dementia, mixed dementia, dementia induced by Alzheimer's disease or Parkinson's disease).

Disclosed are methods for treating and/or preventing a neurodegenerative disease or a neurocognitive disease in a subject in need thereof, the method comprising administering to the subject an effective amount of a compound having a structure represented by a formula:

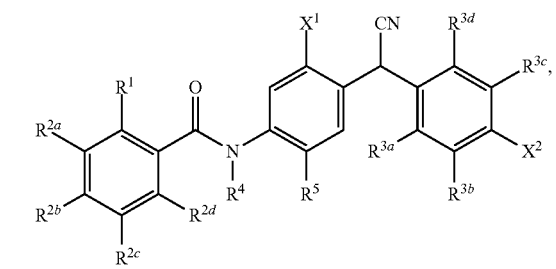

wherein each of $X^1$ and $X^2$ is independently halogen; wherein $R^1$ is selected from —OH, —SR$^{10}$, and —NR$^{11a}$R$^{11b}$; wherein each of $R^{10}$, $R^{11a}$, and $R^{11b}$, when present, is independently selected from hydrogen and C1-C4 alkyl; wherein each of $R^{2a}$, $R^{2b}$, $R^{2c}$, and $R^{2d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino; wherein each of $R^{3a}$, $R^{3b}$, $R^{3c}$, and $R^{3d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino; wherein $R^4$ is selected from hydrogen and C1-C4 alkyl; and wherein $R^5$ is C1-C4 alkyl, provided that the compound is not:

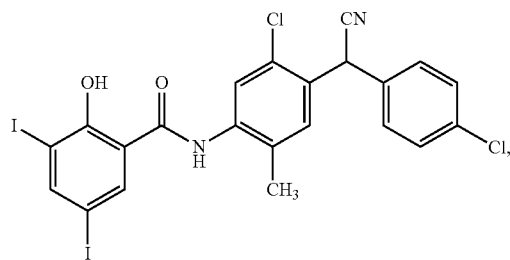 [SMILES: Cc1cc(C(C#N)c2ccc(Cl)cc2)c(Cl)cc1NC(=O)c1cc(I)cc(I)c1O]

or a pharmaceutically acceptable salt thereof.

Also disclosed are methods of treating and/or preventing dementia in a subject in in need thereof, the method comprising administering to the subject an effective amount of a compound having a structure represented by a formula:

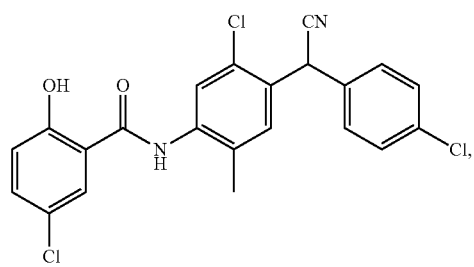 [SMILES: Cc1cc(C(C#N)c2ccc(Cl)cc2)c(Cl)cc1NC(=O)c1cc(Cl)ccc1O]

or a pharmaceutically acceptable salt thereof.

Also disclosed are kits comprising a compound having a structure represented by a formula:

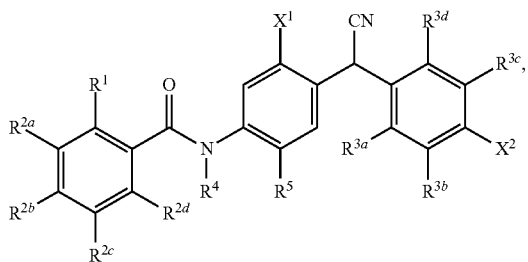

wherein each of $X^1$ and $X^2$ is independently halogen; wherein $R^1$ is selected from —OH, —$SR^{10}$, and —$NR^{11a}R^{11b}$; wherein each of $R^{10}$, $R^{11a}$, and $R^{11b}$, when present, is independently selected from hydrogen and C1-C4 alkyl; wherein each of $R^{2a}$, $R^{2b}$, $R^{2c}$, and $R^{2d}$ is independently selected from hydrogen, halogen, —$NO_2$, —CN, —OH, —SH, —$NH_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino; wherein each of $R^{3a}$, $R^{3b}$, $R^{3c}$, and $R^{3d}$ is independently selected from hydrogen, halogen, —$NO_2$, —CN, —OH, —SH, —$NH_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino; wherein $R^4$ is selected from hydrogen and C1-C4 alkyl; and wherein $R^5$ is C1-C4 alkyl, provided that the compound is not:

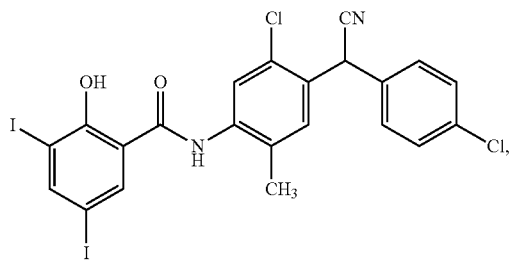 [SMILES: Cc1cc(C(C#N)c2ccc(Cl)cc2)c(Cl)cc1NC(=O)c1cc(I)cc(I)c1O]

or a pharmaceutically acceptable salt thereof, and one or more of: (a) at least one agent associated with the treatment of a neurodegenerative disease; (b) at least one agent associated with the treatment of a neurocognitive disease; (c) instructions for administering the compound in connection with treating a neurodegenerative disease; (d) instructions for administering the compound in connection with treating a neurocognitive disease; (e) instructions for treating a neurodegenerative disease; and (f) instructions for treating a neurocognitive disease.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BRIEF DESCRIPTION OF THE DRAWINGS

The accompanying figures, which are incorporated in and constitute a part of this specification, illustrate several aspects and together with the description serve to explain the principles of the invention.

Figure 1B:
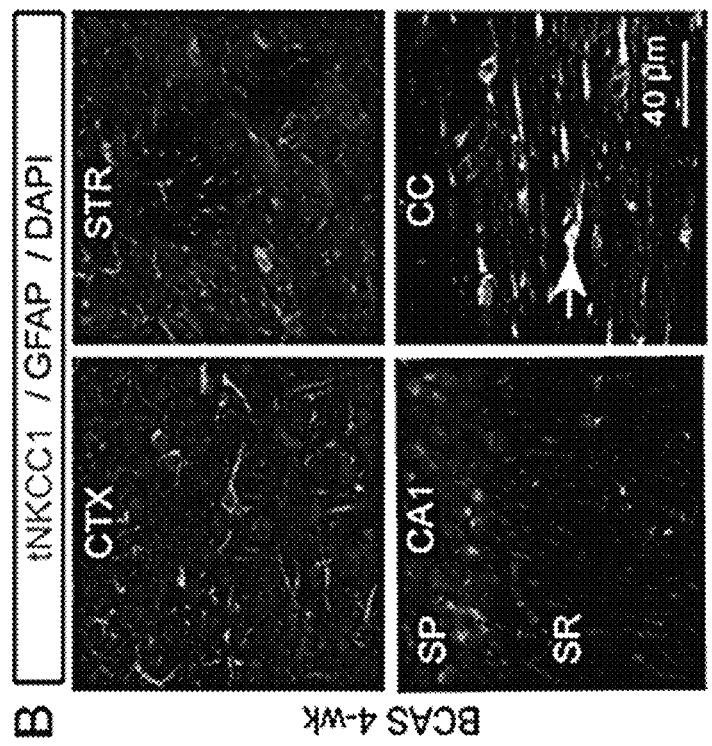
FIG. 1A-D show representative data illustrating total NKCC1 protein expression in mouse brains after bilateral carotid artery stenosis (BCAS).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

Listed below are definitions of various terms used to describe this invention. These definitions apply to the terms as they are used throughout this specification, unless otherwise limited in specific instances, either individually or as part of a larger group.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" mean that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In one aspect, the subject is a mammal. A patient refers to a subject afflicted with a hypoxic brain injury. The term "patient" includes human and veterinary subjects. In some aspects of the disclosed methods, the subject has been diagnosed with a need for treatment of a neurocognitive disorder prior to the administering step. In various aspects, the neurocognitive disorder is dementia (e.g., vascular dementia, frontotemporal dementia, Lewy body dementia, mixed dementia, dementia induced by Alzheimer's disease or Parkinson's disease). In some aspects of the disclosed methods, the subject has been diagnosed with a need for treatment of a neurodegenerative disorder prior to the administering step. In various aspects, the neurodegenerative disorder is selected from Alzheimer's disease, cerebral autosomal dominant arteriopathy with subcortical infarcts and leukoencephalopathy (CADASIL), Parkinson's disease, Huntington's disease, amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia, and Lewy body disease.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the condition from occurring in a subject that can be predisposed to the condition but has not yet been diagnosed as having it; (ii) inhibiting the condition, i.e., arresting its development; or (iii) relieving the condition, i.e., causing regression of the condition. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a hypoxic brain injury prior to the administering step. As used herein, the phrase "identified to be in need of treatment for a disorder," or the like, refers to selection of a subject based upon need for treatment of the disorder or condition. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "treating" refers to relieving the disease, disorder, or condition, i.e., causing regression of the disease, disorder, and/or condition. The term "preventing" refers to preventing a disease, disorder, or condition from occurring in a human or an animal that may be predisposed to the disease, disorder and/or condition, but has not yet been diagnosed as having it; and/or inhibiting the disease, disorder, or condition, i.e., arresting its development.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein.

The term "comprising" (and its grammatical variations) as used herein is used in the inclusive sense of "having" or "including" and not in the exclusive sense of "consisting of."

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and include the physiologically acceptable salts, which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric acid, and the like. Salts derived from organic acids, such as aliphatic mono- and dicarboxylic acids, phenyl substituted alkanoic acids, hydroxyalkanoic and hydroxyalkandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, p-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

It is understood that the compounds of the present disclosure relate to all optical isomers and stereo-isomers at the various possible atoms of the molecule, unless specified otherwise. Compounds may be separated or prepared as their pure enantiomers or diasteriomers by crystallization, chromatography or synthesis.

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$A^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —$N(\text{-alkyl})_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —$OC(O)A^1$ or —$C(O)OA^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -$(A^1O(O)C\text{-}A^2\text{-}C(O)O)_a$— or -$(A^1O(O)C\text{-}A^2\text{-}OC(O))_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -$(A^1O\text{-}A^2O)_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^●$, -(halo$R^●$), —$(CH_2)_{0-2}OH$, —$(CH_2)_{0-2}OR^●$, —$(CH_2)_{0-2}CH(OR^●)_2$; —O(halo$R^●$), —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —$(C_{1-4}$ straight or branched alkylene)C(O)O$R^●$, or —$SSR^●$ wherein each $R^●$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "organic residue" defines a carbon-containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

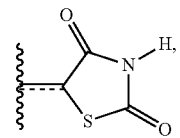

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. "Solvates" refers to the compound formed by the interaction of a solvent and a solute and includes hydrates. Solvates are usually crystalline solid adducts containing solvent molecules within the crystal structure, in either stoichiometric or nonstoichiometric proportions. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules, which owe their stability through non-covalent interaction. One or more components of this molecular complex provide a stable framework in the crystalline lattice. In certain instances, the guest molecules are incorporated in the crystalline lattice as anhydrates or solvates, see, e.g., "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids, which are present in different states of order, which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

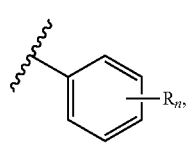

which is understood to be equivalent to a formula:

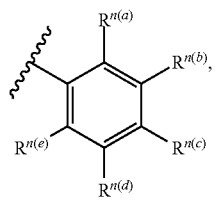

wherein n is typically an integer. That is, R" is understood to represent five independent substituents, $R^{n(a)}$, $R^{n(b)}$, $R^{n(c)}$, $R^{n(d)}$, $R^{n(e)}$. In each such case, each of the five R" can be hydrogen or a recited substituent. By "independent substituents," it is meant that each R substituent can be independently defined. For example, if in one instance $R^{n(a)}$ is halogen, then $R^{n(b)}$ is not necessarily halogen in that instance.

In some yet further aspects, a structure of a compound can be represented by a formula:

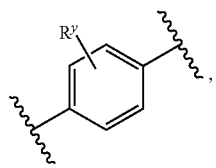

wherein $R^y$ represents, for example, 0-2 independent substituents selected from $A^1$, $A^2$, and $A^3$, which is understood to be equivalent to the groups of formulae:

wherein $R^y$ represents 0 independent substituents

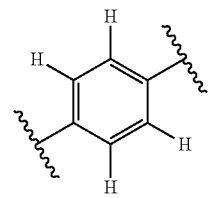

wherein $R^y$ represents 1 independent substituent

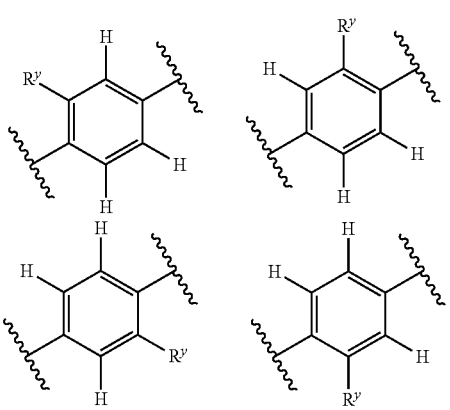

wherein $R^y$ represents 2 independent substituents

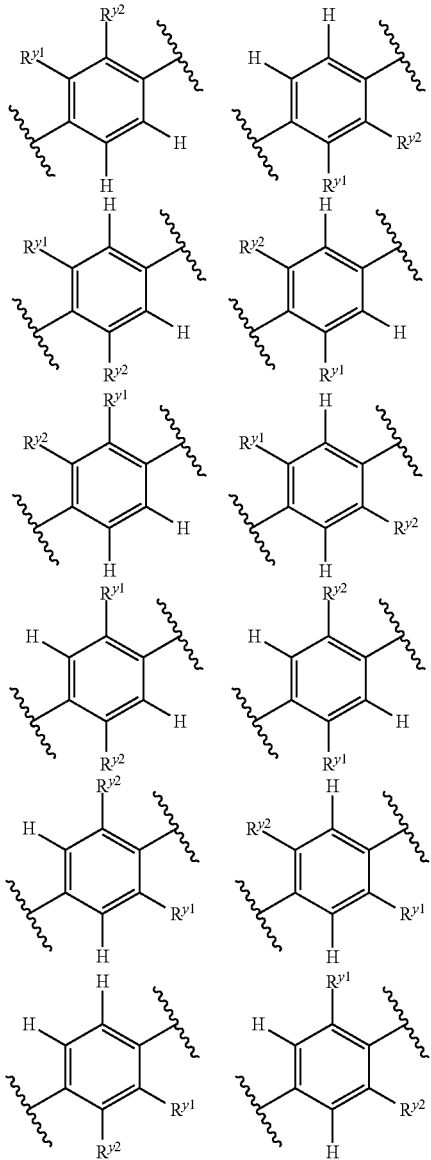

Again, by "independent substituents," it is meant that each R substituent can be independently defined. For example, if in one instance $R^{y1}$ is $A^1$, then $R^{y2}$ is not necessarily $A^1$ in that instance.

In some further aspects, a structure of a compound can be represented by a formula,

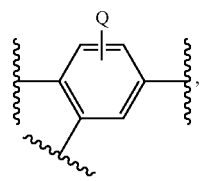

wherein, for example, Q comprises three substituents independently selected from hydrogen and A, which is understood to be equivalent to a formula:

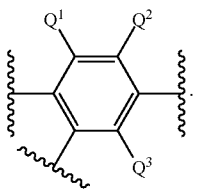

Again, by "independent substituents," it is meant that each Q substituent is independently defined as hydrogen or A, which is understood to be equivalent to the groups of formulae:

wherein Q comprises three substituents independently selected from H and A

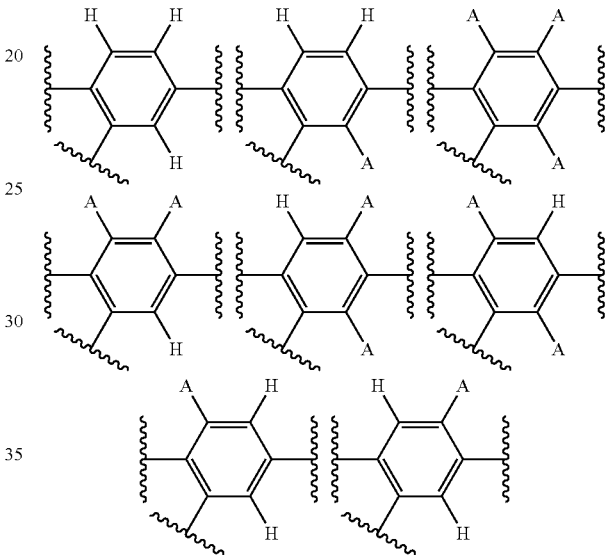

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, disclosed are substituted N-(5-chloro-4-((4-chlorophenyl)(cyano)methyl)-2-methylphenyl)benzamide compounds useful in the treatment and/or prevention of neurodegenerative or neurocognitive disorders including, but not limited to, Alzheimer's disease, cerebral autosomal dominant arteriopathy with sub-cortical infarcts and leukoencephalopathy (CADASIL), Parkinson's disease, Huntington's disease, amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia, Lewy body disease, and dementia (e.g., vascular dementia, Lewy body dementia, frontotemporal dementia, mixed dementia, dementia induced by Alzheimer's disease or Parkinson's disease).

In one aspect, the disclosed compounds exhibit modification of SPAK kinase function. In a further aspect, the disclosed compounds exhibit inhibition of SPAK kinase function.

In one aspect, the disclosed compounds are useful in inhibiting SPAK kinase function in a mammal. In a further aspect, the disclosed compounds are useful in inhibiting SPAK kinase function in at least one cell.

In one aspect, the disclosed compounds are useful in the treatment and/or prevention of neurodegenerative or neurocognitive diseases, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

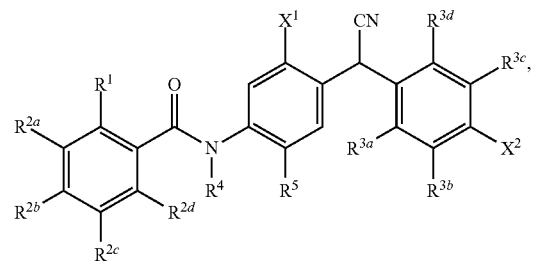

wherein each of $X^1$ and $X^2$ is independently halogen; wherein $R^1$ is selected from —OH, —SR$^{10}$, and —NR$^{11a}$R$^{11b}$; wherein each of $R^{10}$, $R^{11a}$, and $R^{11b}$, when present, is independently selected from hydrogen and C1-C4 alkyl; wherein each of $R^{2a}$, $R^{2b}$, $R^{2c}$, and $R^{2d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino; wherein each of $R^{3a}$, $R^{3b}$, $R^{3c}$, and $R^{3d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino; wherein $R^4$ is selected from hydrogen and C1-C4 alkyl; and wherein $R^5$ is C1-C4 alkyl, provided that the compound is not:

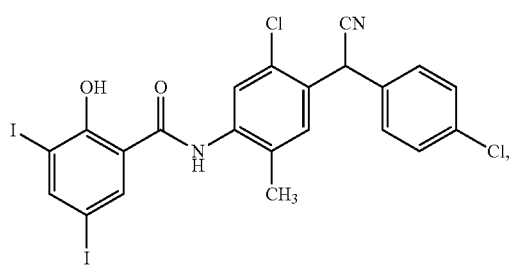

or a pharmaceutically acceptable salt thereof.

In one aspect, disclosed are compounds having a structure represented by a formula:

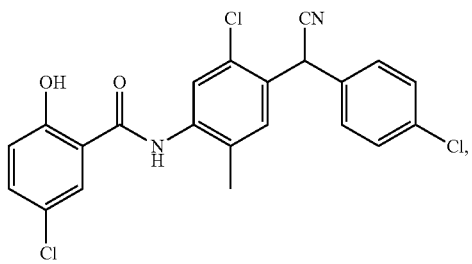

or a pharmaceutically acceptable salt thereof.

In a further aspect, the compound has a structure represented by a formula:

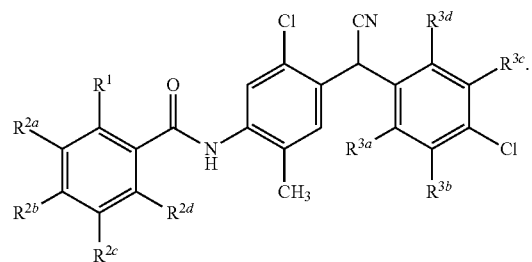

In a further aspect, the compound has a structure represented by a formula:

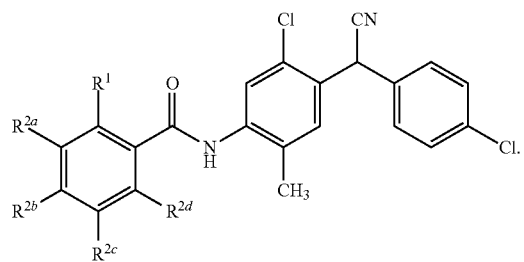

In a further aspect, the compound has a structure represented by a formula:

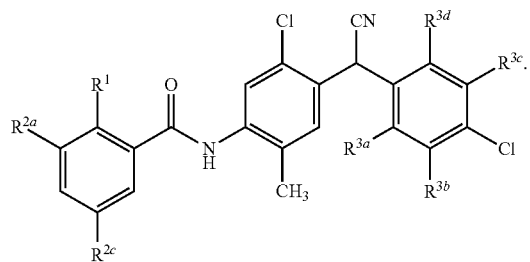

In a further aspect, the compound has a structure represented by a formula:

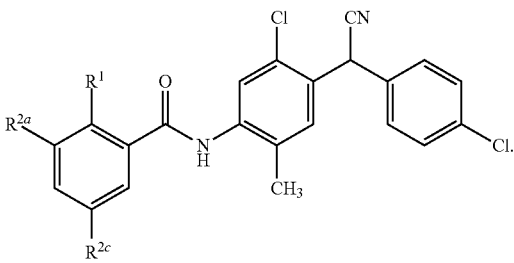

In a further aspect, the compound has a structure represented by a formula:

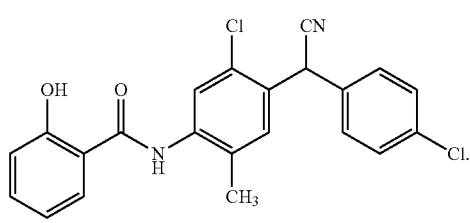 [SMILES: Cc1cc(C(C#N)c2ccc(Cl)cc2)c(Cl)cc1NC(=O)c1ccccc1O]

In a further aspect, the compound has a structure represented by a formula:

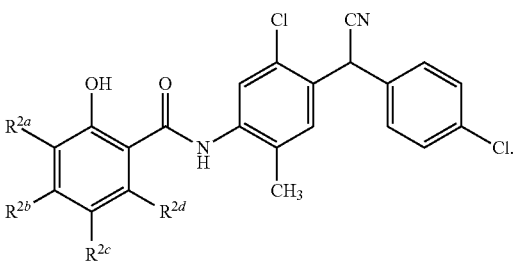

In a further aspect, the compound is selected from:

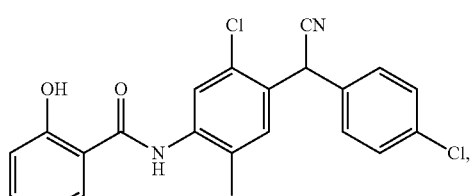

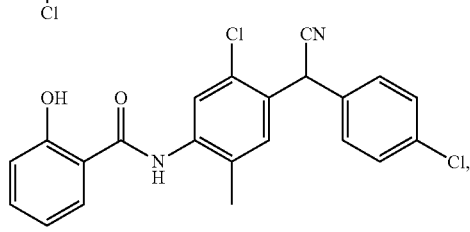

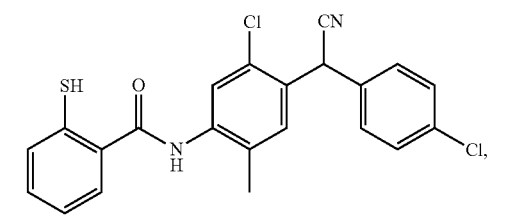
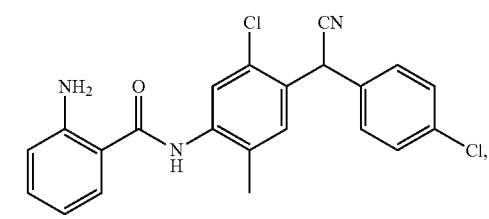
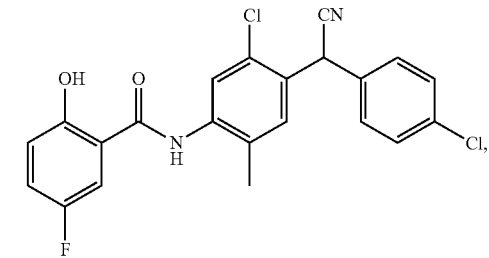
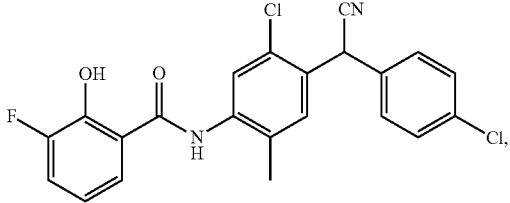
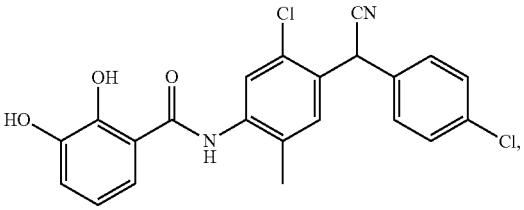
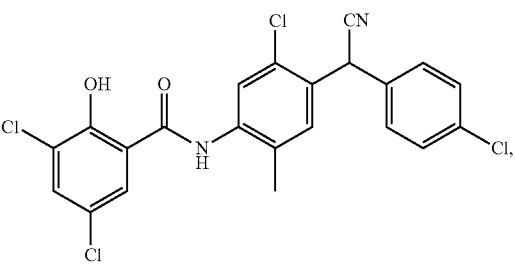
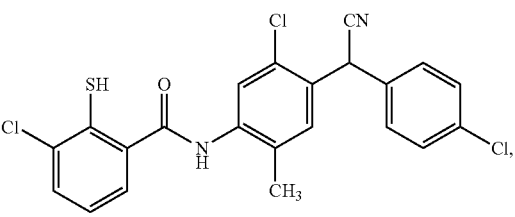
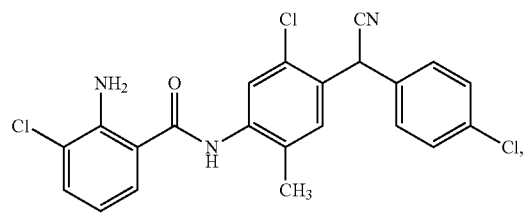
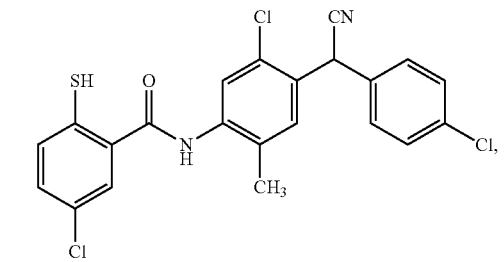
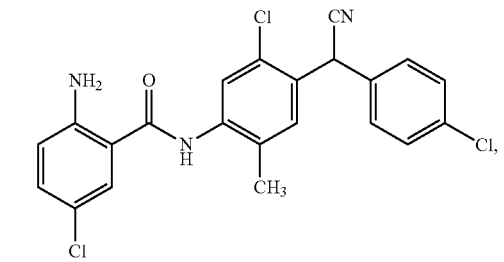
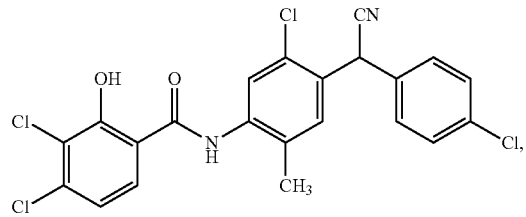
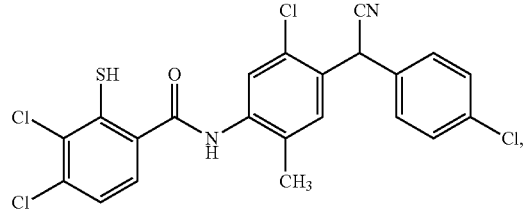
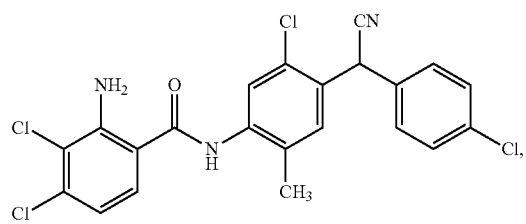
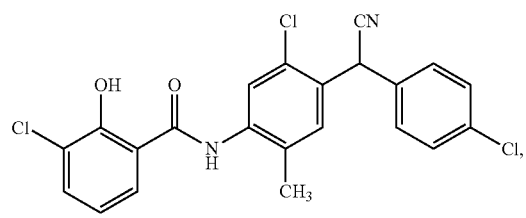

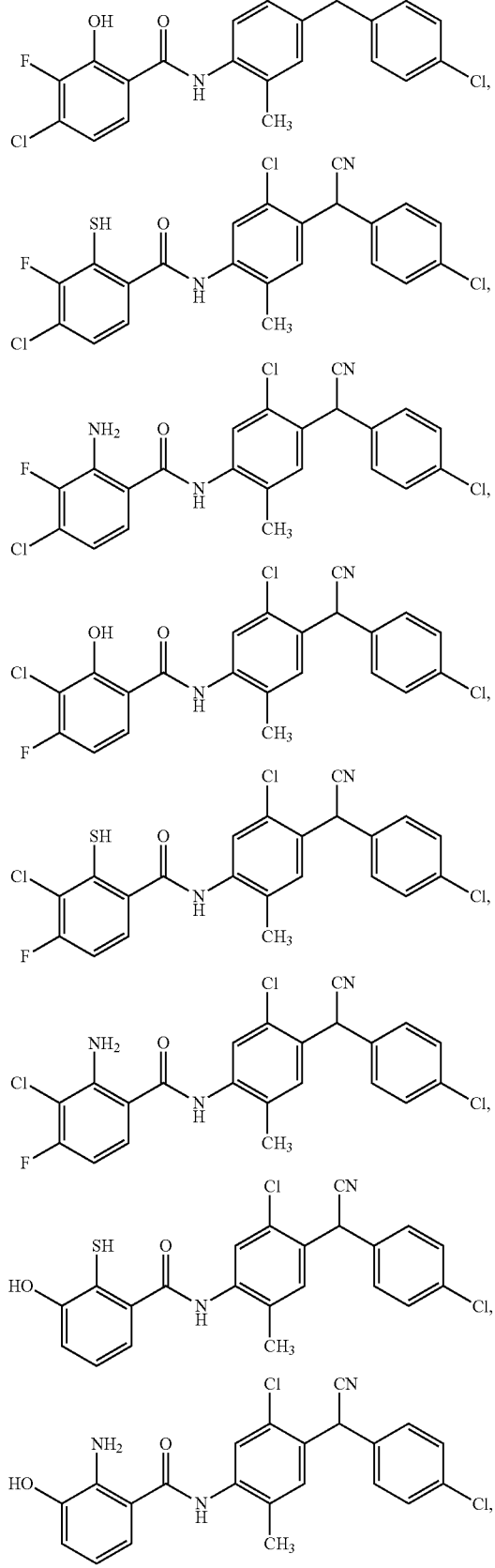
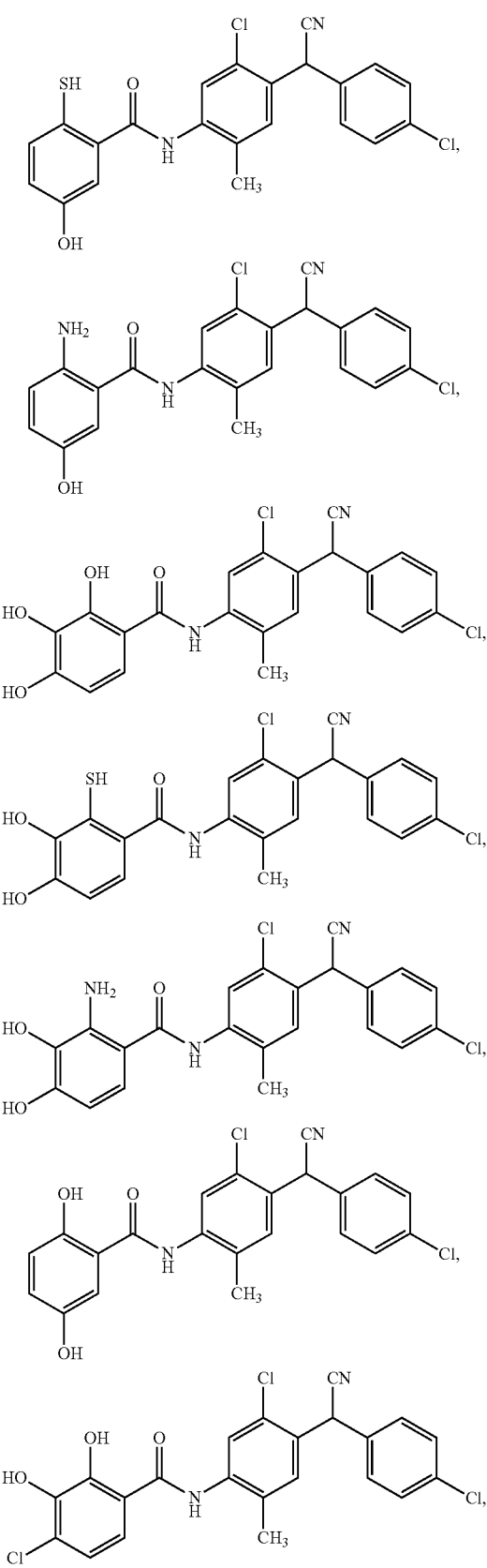

-continued

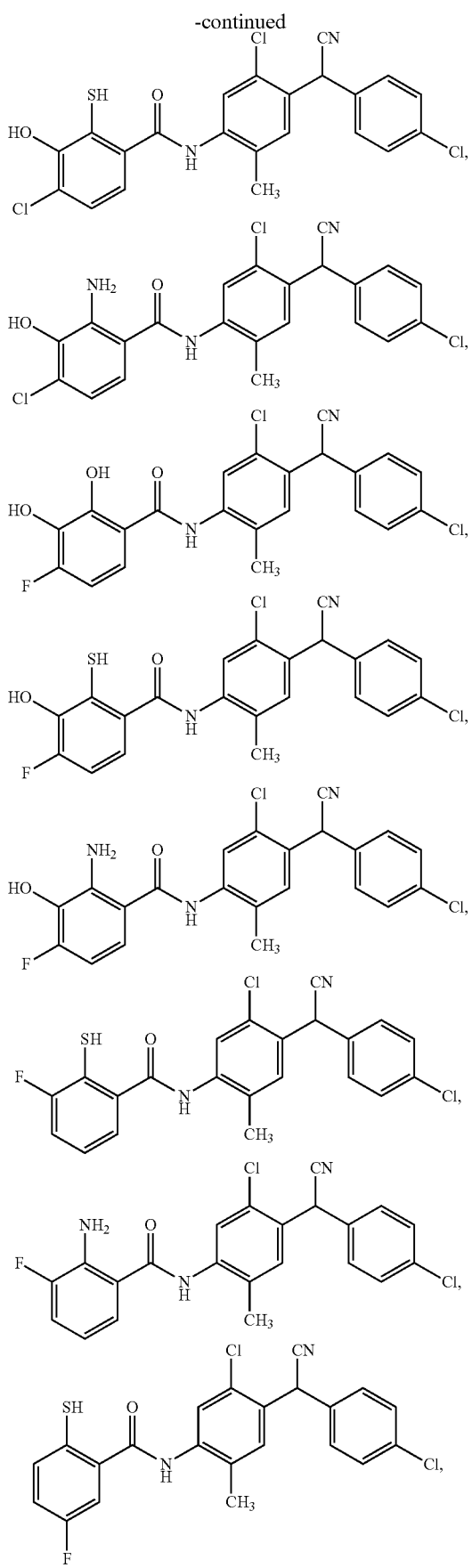

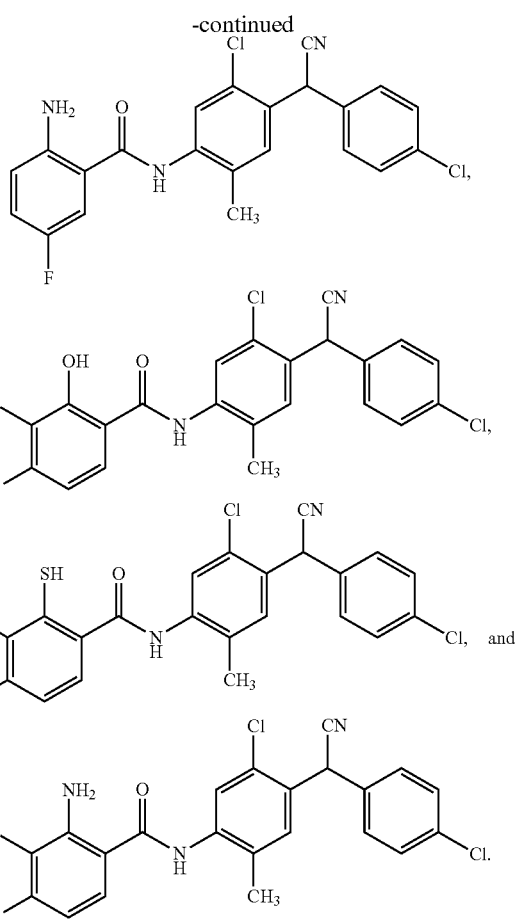

A. $X^1$ and $X^2$ Groups

In one aspect, each of $X^1$ and $X^2$ are independently halogen. In a further aspect, each of $X^1$ and $X^2$ are independently selected from —Cl, —Br, and —F. In a still further aspect, each of $X^1$ and $X^2$ are independently selected from —Cl and —Br. In yet a further aspect, each of $X^1$ and X2 are independently selected from —Cl and —F. In an even further aspect, each of $X^1$ and $X^2$ are independently selected from —Br and —F.

In various aspects, each of $X^1$ and $X^2$ are the same halogen. In various further aspects, each of $X^1$ and $X^2$ are different halogen.

In various aspects, each of $X^1$ and $X^2$ are —I. In a further aspect, each of $X^1$ and $X^2$ are —I. In a still further aspect, each of $X^1$ and $X^2$ are —Br. In yet a further aspect, each of $X^1$ and X2 are —Cl. In an even further aspect, each of $X^1$ and $X^2$ are —F.

b. $R^1$ Groups

In one aspect, $R^1$ is selected from —OH, —SR$^{10}$, and —NR$^{11a}$R$^{11b}$. In a further aspect, $R^1$ is selected from —OH and —SR$^{10}$. In a still further aspect, $R^1$ is selected from —SR$^{10}$ and —NR$^{11a}$R$^{11b}$. In yet a further aspect, $R^1$ is selected from —OH and —NR$^{11a}$R$^{11b}$. In an even further aspect, $R^1$ is —OH. In a still further aspect, $R^1$ is —SR$^{10}$. In yet a further aspect, $R^1$ is —NR$^{11a}$R$^{11b}$.

c. $R^{2a}$, $R^{2b}$, $R^{2c}$, and $R^{2d}$ Groups

In one aspect, each of $R^{2a}$, $R^{2b}$, $R^{2c}$, and $R^{2d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino. In a further aspect, each of $R^{2a}$, $R^{2b}$, $R^{2c}$, and $R^{2d}$ is hydrogen.

In a further aspect, each of $R^{2b}$ and $R^{2d}$ is hydrogen. In a still further aspect, each of $R^{2a}$ and $R^{2c}$ is not hydrogen. In yet a further aspect, at least one of $R^{2a}$ and $R^{2c}$ is not hydrogen.

In a further aspect, each of $R^{2a}$, $R^{2b}$, $R^{2c}$, and $R^{2d}$ is independently selected from hydrogen, halogen, —$NO_2$, —CN, —OH, —SH, —$NH_2$, C1-C4 alkyl, and C1-C4 haloalkyl. In a still further aspect, each of $R^{2a}$, $R^{2b}$, $R^{2c}$, and $R^{2d}$ is independently selected from hydrogen, —F, —Cl, —$NO_2$, —CN, —OH, —SH, —$NH_2$, methyl, ethyl, n-propyl, i-propyl, —$CH_2Cl$, —$CH_2CH_2Cl$, —$CH_2CH_2CH_2Cl$, —$CH(CH_2Cl)(CH_3)$, —$CH_2F$, —$CH_2CH_2F$, —$CH_2CH_2CH_2F$, and —$CH(CH_2F)(CH_3)$. In yet a further aspect, each of $R^{2a}$, $R^{2b}$, $R^{2c}$, and $R^{2d}$ is independently selected from hydrogen, —F, —Cl, —$NO_2$, —CN, —OH, —SH, —$NH_2$, methyl, ethyl, —$CH_2Cl$, —$CH_2CH_2Cl$, —$CH_2F$, and —$CH_2CH_2F$. In an even further aspect, each of $R^{2a}$, $R^{2b}$, $R^{2c}$, and $R^{2d}$ is independently selected from hydrogen, —F, —Cl, —$NO_2$, —CN, —OH, —SH, —$NH_2$, —$CH_2Cl$, and —$CH_2F$.

In a further aspect, each of $R^{2a}$, $R^{2b}$, $R^{2c}$, and $R^{2d}$ is independently selected from hydrogen, halogen, —$NO_2$, —CN, —OH, —SH, and —$NH_2$. In a still further aspect, each of $R^{2a}$, $R^{2b}$, $R^{2c}$, and $R^{2d}$ is independently selected from hydrogen, —F, —Cl, —$NO_2$, —CN, —OH, —SH, and —$NH_2$. In yet a further aspect, each of $R^{2a}$, $R^{2b}$, $R^{2c}$, and $R^{2d}$ is independently selected from hydrogen, —F, —Cl, —OH, —SH, and —$NH_2$. In an even further aspect, each of $R^{2a}$, $R^{2b}$, $R^{2c}$, and $R^{2d}$ is independently selected from hydrogen, —F, —Cl, and —OH.

In a further aspect, each of $R^{2a}$, $R^{2b}$, $R^{2c}$, and $R^{2d}$ is independently selected from hydrogen, C1-C4 alkyl, and C1-C4 haloalkyl. In a still further aspect, each of $R^{2a}$, $R^{2b}$, $R^{2c}$, and $R^{2d}$ is independently selected from hydrogen, methyl, ethyl, n-propyl, i-propyl, —$CH_2Cl$, —$CH_2CH_2Cl$, —$CH_2CH_2CH_2Cl$, —$CH(CH_2Cl)(CH_3)$, —$CH_2F$, —$CH_2CH_2F$, —$CH_2CH_2CH_2F$, and —$CH(CH_2F)(CH_3)$. In yet a further aspect, each of $R^{2a}$, $R^{2b}$, $R^{2c}$, and $R^{2d}$ is independently selected from hydrogen, methyl, ethyl, —$CH_2Cl$, —$CH_2CH_2Cl$, —$CH_2F$, and —$CH_2CH_2F$. In an even further aspect, each of $R^{2a}$, $R^{2b}$, $R^{2c}$, and $R^{2d}$ is independently selected from hydrogen, —$CH_2Cl$, and —$CH_2F$.

In a further aspect, each of $R^{2a}$, $R^{2b}$, $R^{2c}$, and $R^{2d}$ is independently selected from hydrogen, halogen, and C1-C4 alkyl. In a still further aspect, each of $R^{2a}$, $R^{2b}$, $R^{2c}$, and $R^{2d}$ is independently selected from hydrogen, methyl, ethyl, n-propyl, and i-propyl. In yet a further aspect, each of $R^{2a}$, $R^{2b}$, $R^{2c}$, and $R^{2d}$ is independently selected from hydrogen, halogen, methyl, and ethyl. In an even further aspect, each of $R^{2a}$, $R^{2b}$, $R^{2c}$, and $R^{2d}$ is independently selected from hydrogen, halogen, and ethyl. In a still further aspect, each of $R^{2a}$, $R^{2b}$, $R^{2c}$, and $R^d$ is independently selected from hydrogen, halogen, and methyl.

In a further aspect, each of $R^{2a}$, $R^{2b}$, $R^{2c}$, and $R^{2d}$ is independently selected from hydrogen, halogen, and C1-C4 haloalkyl. In a still further aspect, each of $R^{2a}$, $R^{2b}$, $R^{2c}$, and $R^{2d}$ is independently selected from hydrogen, —F, —Cl, —$CH_2Cl$, —$CH_2CH_2Cl$, —$CH_2CH_2CH_2Cl$, —$CH(CH_2Cl)(CH_3)$, —$CH_2F$, —$CH_2CH_2F$, —$CH_2CH_2CH_2F$, and —$CH(CH_2F)(CH_3)$. In yet a further aspect, each of $R^{2a}$, $R^{2b}$, $R^{2c}$, and $R^{2d}$ is independently selected from hydrogen, —F, —Cl, —$CH_2Cl$, —$CH_2CH_2Cl$, —$CH_2F$, and —$CH_2CH_2F$. In an even further aspect, each of $R^{2a}$, $R^{2b}$, $R^{2c}$, and $R^{2d}$ is independently selected from hydrogen, —F, —Cl, —$CH_2Cl$, and —$CH_2F$.

In a further aspect, each of $R^{2a}$, $R^{2b}$, $R^{2c}$, and $R^{2d}$ is independently selected from hydrogen and halogen. In a still further aspect, each of $R^{2a}$, $R^{2b}$, $R^{2c}$, and $R^{2d}$ is independently selected from hydrogen, —F, —Cl, and —Br. In yet a further aspect, each of $R^{2a}$, $R^{2b}$, $R^{2c}$, and $R^{2d}$ is independently selected from hydrogen, —F, and —Cl. In an even further aspect, each of $R^{2a}$, $R^{2b}$, $R^{2c}$, and $R^{2d}$ is independently selected from hydrogen and —F. In a still further aspect, each of $R^{2a}$, $R^{2b}$, $R^{2c}$, and $R^{2d}$ is independently selected from hydrogen and —Cl.

d. $R^{3a}$, $R^{3b}$, $R^{3c}$, and $R^{3d}$ Groups

In one aspect, each of $R^{3a}$, $R^{3b}$, $R^{3c}$, and $R^{3d}$ is independently selected from hydrogen, halogen, —$NO_2$, —CN, —OH, —SH, —$NH_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino. In a further aspect, each of $R^{3a}$, $R^{3b}$, $R^{3c}$, and $R^{3d}$ is hydrogen.

In a further aspect, each of $R^{3b}$ and $R^{3d}$ is hydrogen. In a still further aspect, each of $R^{3a}$ and $R^{3c}$ is not hydrogen. In yet a further aspect, at least one of $R^{3a}$ and $R^{3c}$ is not hydrogen.

In a further aspect, each of $R^{3a}$, $R^{3b}$, $R^{3c}$, and $R^{3d}$ is independently selected from hydrogen, halogen, —$NO_2$, —CN, —OH, —SH, —$NH_2$, C1-C4 alkyl, and C1-C4 haloalkyl. In a still further aspect, each of $R^{3a}$, $R^{3b}$, $R^{3c}$, and $R^{3d}$ is independently selected from hydrogen, —F, —Cl, —$NO_2$, —CN, —OH, —SH, —$NH_2$, methyl, ethyl, n-propyl, i-propyl, —$CH_2Cl$, —$CH_2CH_2Cl$, —$CH_2CH_2CH_2Cl$, —$CH(CH_2Cl)(CH_3)$, —$CH_2F$, —$CH_2CH_2F$, —$CH_2CH_2CH_2F$, and —$CH(CH_2F)(CH_3)$. In yet a further aspect, each of $R^{3a}$, $R^{3b}$, $R^{3c}$, and $R^{3d}$ is independently selected from hydrogen, —F, —Cl, —$NO_2$, —CN, —OH, —SH, —$NH_2$, methyl, ethyl, —$CH_2Cl$, —$CH_2CH_2Cl$, —$CH_2F$, and —$CH_2CH_2F$. In an even further aspect, each of $R^{3a}$, $R^{3b}$, $R^{3c}$, and $R^{3d}$ is independently selected from hydrogen, —F, —Cl, —$NO_2$, —CN, —OH, —SH, —$NH_2$, —$CH_2Cl$, and —$CH_2F$.

In a further aspect, each of $R^{3a}$, $R^{3b}$, $R^{3c}$, and $R^{3d}$ is independently selected from hydrogen, halogen, —$NO_2$, —CN, —OH, —SH, and —$NH_2$. In a still further aspect, each of $R^{3a}$, $R^{3b}$, $R^{3c}$, and $R^{3d}$ is independently selected from hydrogen, —F, —Cl, —$NO_2$, —CN, —OH, —SH, and —$NH_2$. In yet a further aspect, each of $R^{3a}$, $R^{3b}$, $R^{3c}$, and $R^{3d}$ is independently selected from hydrogen, —F, —Cl, —OH, —SH, and —$NH_2$. In an even further aspect, each of $R^{3a}$, $R^{3b}$, $R^{3c}$, and $R^{3d}$ is independently selected from hydrogen, —F, —Cl, and —OH.

In a further aspect, each of $R^{3a}$, $R^{3b}$, $R^{3c}$, and $R^{3d}$ is independently selected from hydrogen, C1-C4 alkyl, and C1-C4 haloalkyl. In a still further aspect, each of $R^{3a}$, $R^{3b}$, $R^{3c}$, and $R^{3d}$ is independently selected from hydrogen, methyl, ethyl, n-propyl, i-propyl, —$CH_2Cl$, —$CH_2CH_2Cl$, —$CH_2CH_2CH_2Cl$, —$CH(CH_2Cl)(CH_3)$, —$CH_2F$, —$CH_2CH_2F$, —$CH_2CH_2CH_2F$, and —$CH(CH_2F)(CH_3)$. In yet a further aspect, each of $R^{3a}$, $R^{3b}$, $R^{3c}$, and $R^{3d}$ is independently selected from hydrogen, methyl, ethyl, —$CH_2Cl$, —$CH_2CH_2Cl$, —$CH_2F$, and —$CH_2CH_2F$. In an even further aspect, each of $R^{3a}$, $R^{3b}$, $R^{3c}$, and $R^{3d}$ is independently selected from hydrogen, —$CH_2Cl$, and —$CH_2F$.

In a further aspect, each of $R^{3a}$, $R^{3b}$, $R^{3c}$, and $R^{3d}$ is independently selected from hydrogen, halogen, and C1-C4 alkyl. In a still further aspect, each of $R^{3a}$, $R^{3b}$, $R^{3c}$, and $R^{3d}$ is independently selected from hydrogen, methyl, ethyl, n-propyl, and i-propyl. In yet a further aspect, each of $R^{3a}$, $R^{3b}$, $R^{3c}$, and $R^{3d}$ is independently selected from hydrogen, halogen, methyl, and ethyl. In an even further aspect, each of $R^{3a}$, $R^{3b}$, $R^{3c}$, and $R^{3d}$ is independently selected from hydrogen, halogen, and ethyl. In a still further aspect, each of v independently selected from hydrogen, halogen, and methyl.

In a further aspect, each of $R^{3a}$, $R^{3b}$, $R^{3c}$, and $R^{3d}$ is independently selected from hydrogen, halogen, and C1-C4 haloalkyl. In a still further aspect, each of $R^{3a}$, $R^{3b}$, $R^{3c}$, and $R^{3d}$ is independently selected from hydrogen, —F, —Cl, —CH$_2$Cl, —CH$_2$CH$_2$Cl, —CH$_2$CH$_2$CH$_2$Cl, —CH(CH$_2$Cl) (CH$_3$), —CH$_2$F, —CH$_2$CH$_2$F, —CH$_2$CH$_2$CH$_2$F, and —CH (CH$_2$F)(CH$_3$). In yet a further aspect, each of $R^{3a}$, $R^{3b}$, $R^{3c}$, and $R^{3d}$ is independently selected from hydrogen, —F, —Cl, —CH$_2$Cl, —CH$_2$CH$_2$Cl, —CH$_2$F, and —CH$_2$CH$_2$F. In an even further aspect, each of $R^{3a}$, $R^{3b}$, $R^{3c}$, and $R^{3d}$ is independently selected from hydrogen, —F, —Cl, —CH$_2$Cl, and —CH$_2$F.

In a further aspect, each of $R^{3a}$, $R^{3b}$, $R^{3c}$, and $R^{3d}$ is independently selected from hydrogen and halogen. In a still further aspect, each of $R^{3a}$, $R^{3b}$, $R^{3c}$, and $R^{3d}$ is independently selected from hydrogen, —F, —Cl, and —Br. In yet a further aspect, each of $R^{3a}$, $R^{3b}$, $R^{3c}$, and $R^{3d}$ is independently selected from hydrogen, —F, and —Cl. In an even further aspect, each of $R^{3a}$, $R^{3b}$, $R^{3c}$, and $R^{3d}$ is independently selected from hydrogen and —F. In a still further aspect, each of $R^{3a}$, $R^{3b}$, $R^{3c}$, and $R^{3d}$ is independently selected from hydrogen and —Cl.

e. $R^4$ Groups

In one aspect, $R^4$ is selected from hydrogen and C1-C4 alkyl. In a further aspect, $R^4$ is selected from hydrogen, methyl, ethyl, n-propyl, and isopropyl. In a still further aspect, $R^4$ is selected from hydrogen, methyl, and ethyl. In yet a further aspect, $R^4$ is selected from hydrogen and ethyl. In an even further aspect, $R^4$ is selected from hydrogen and methyl.

In various aspects, $R^4$ is C1-C4 alkyl. In a further aspect, $R^4$ is selected from methyl, ethyl, n-propyl, and isopropyl. In a still further aspect, $R^4$ is selected from methyl and ethyl. In yet a further aspect, $R^4$ is ethyl. In an even further aspect, $R^4$ is methyl.

In various aspects, $R^4$ is hydrogen.

f. $R^5$ Groups

In one aspect, $R^5$ is C1-C4 alkyl. In a further aspect, $R^5$ is selected from methyl, ethyl, n-propyl, and isopropyl. In a still further aspect, $R^5$ is selected from methyl and ethyl. In yet a further aspect, $R^5$ is ethyl. In an even further aspect, $R^5$ is methyl.

g. $R^{10}$, $R^{11a}$, and $R^{11d}$ Groups

In one aspect, each of $R^{10}$, $R^{11a}$, and $R^{11b}$, when present, is independently selected from hydrogen and C1-C4 alkyl. In a further aspect, each of $R^{10}$, $R^{11a}$, and $R^{11b}$, when present, is independently selected from hydrogen, methyl, ethyl, n-propyl, and isopropyl. In a still further aspect, each of $R^{10}$, $R^{11a}$, and $R^{11b}$, when present, is independently selected from hydrogen, methyl, and ethyl. In yet a further aspect, each of $R^{10}$, $R^{11a}$, and $R^{11b}$, when present, is independently selected from hydrogen and methyl.

In various aspects, each of $R^{10}$, $R^{11a}$, and $R^{11b}$, when present, is hydrogen.

In various aspects, each of $R^{10}$, $R^{11a}$, and $R^{11b}$, when present, is C1-C4 alkyl. In a further aspect, each of $R^{10}$, $R^{11a}$, and $R^{11b}$, when present, is independently selected from methyl, ethyl, n-propyl, and isopropyl. In a still further aspect, each of $R^{10}$, $R^{11a}$, and $R^{11b}$, when present, is independently selected from methyl and ethyl. In yet a further aspect, each of $R^{10}$, $R^{11a}$, and $R^{11b}$, when present, is methyl.

2. Example Compounds

In one aspect, a compound can be present as one or more of the following structures:

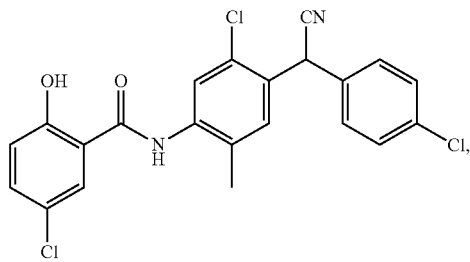 [SMILES: Cc1cc(C(C#N)c2ccc(Cl)cc2)c(Cl)cc1NC(=O)c1cc(Cl)ccc1O]

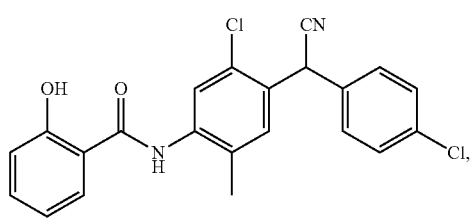

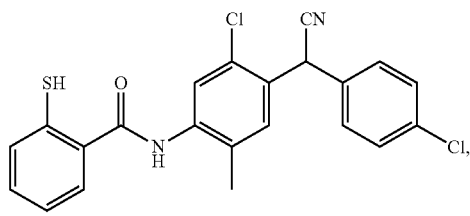

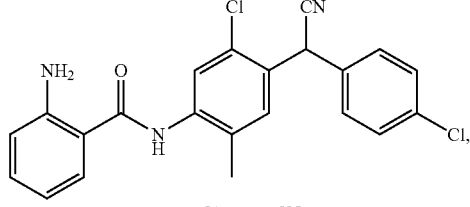

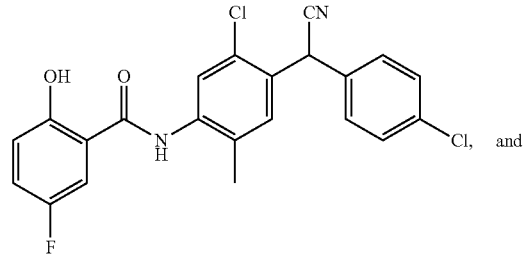

and

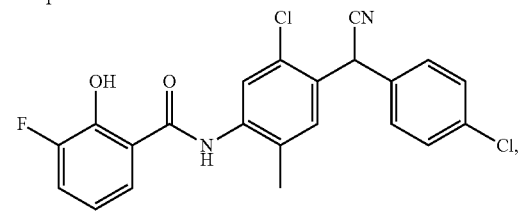

or a pharmaceutically acceptable salt thereof.

In one aspect, a compound can be present as:

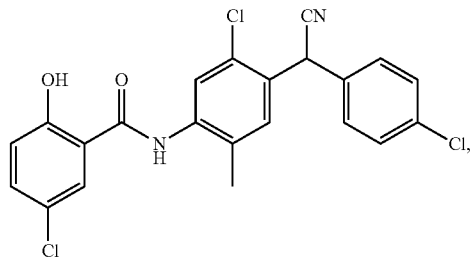

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as inhibitors of SPAK kinase function, and such activity can be determined using the assay methods described herein.

In one aspect, a compound can be selected from:

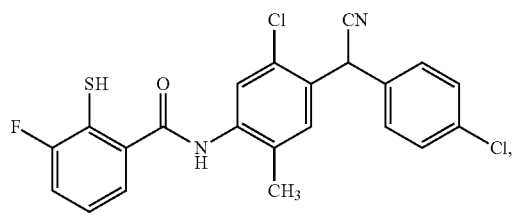

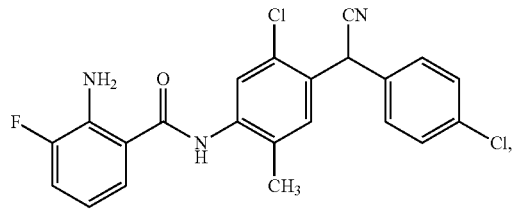

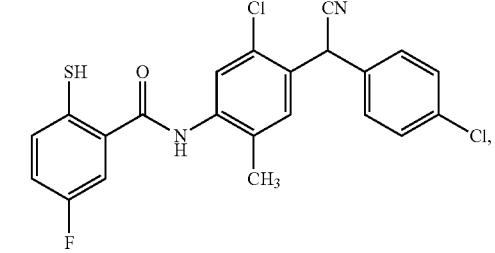

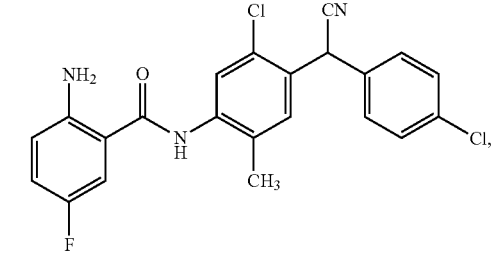

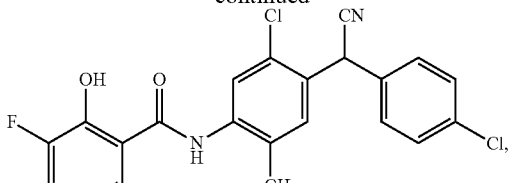

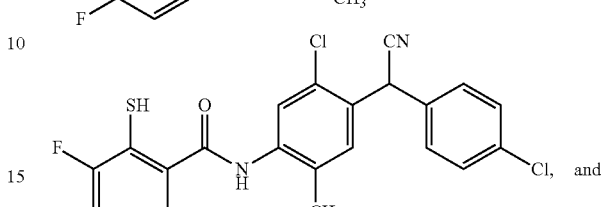

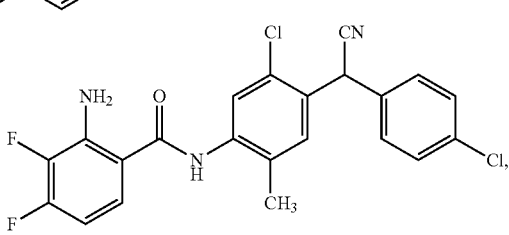

or a pharmaceutically acceptable salt thereof.

In one aspect, a compound can be selected from:

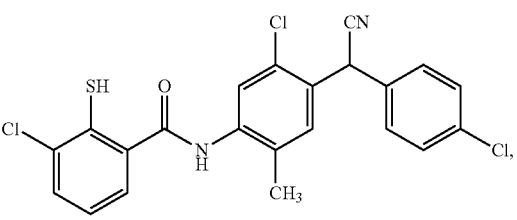

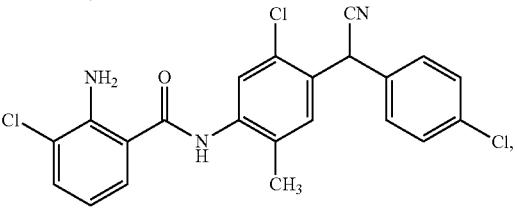 [SMILES: Cc1cc(C(C#N)c2ccc(Cl)cc2)c(Cl)cc1NC(=O)c1cccc(Cl)c1O]

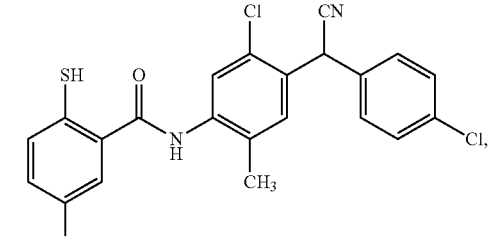

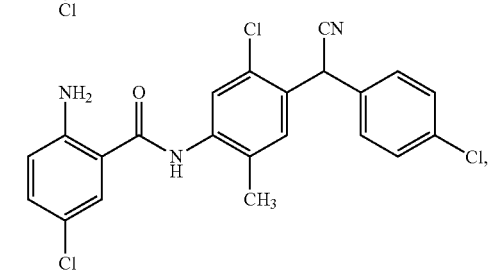

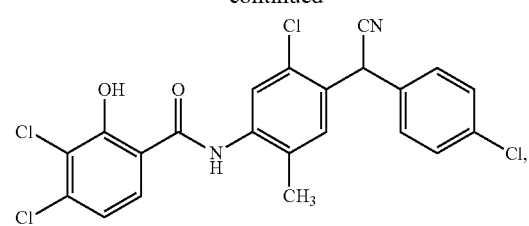
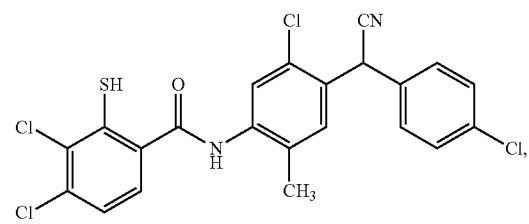
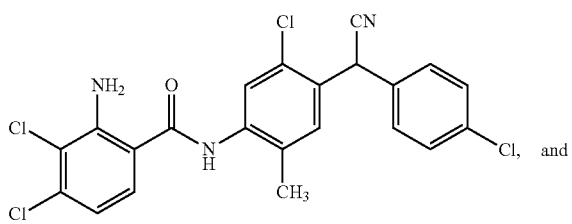
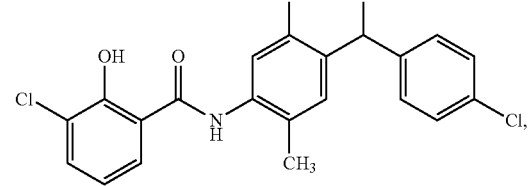
or a pharmaceutically acceptable salt thereof.
In one aspect, a compound can be selected from:
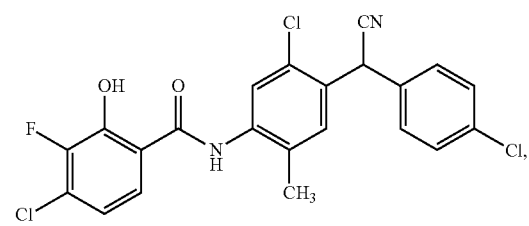
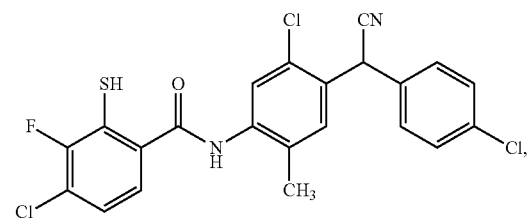
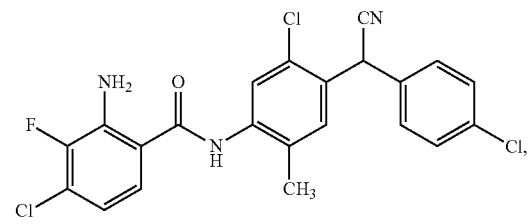
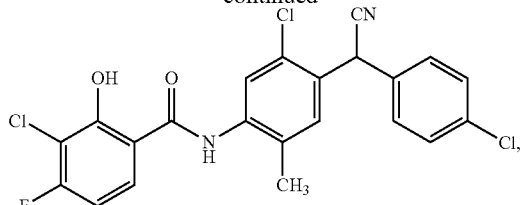
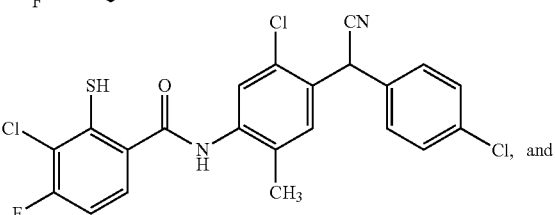
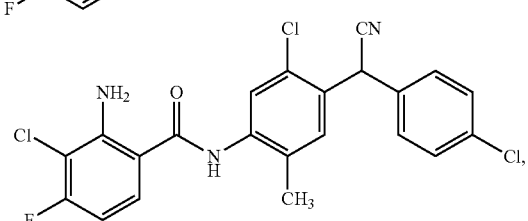
or a pharmaceutically acceptable salt thereof.
In one aspect, a compound can be selected from:
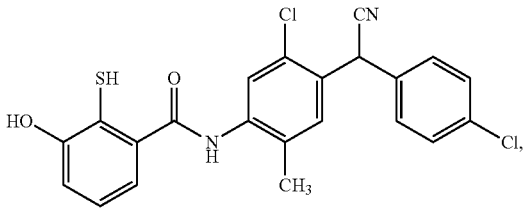
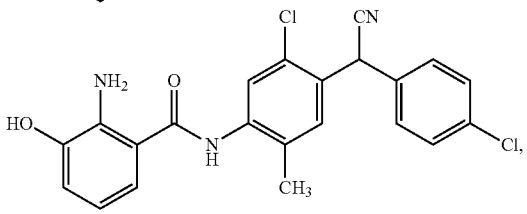
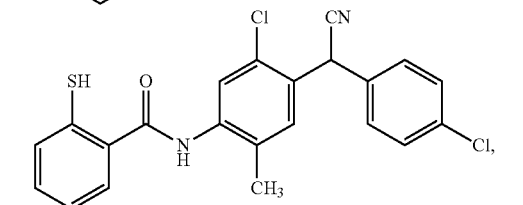
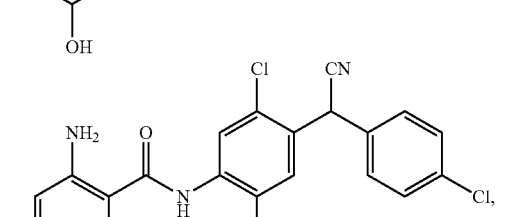

-continued

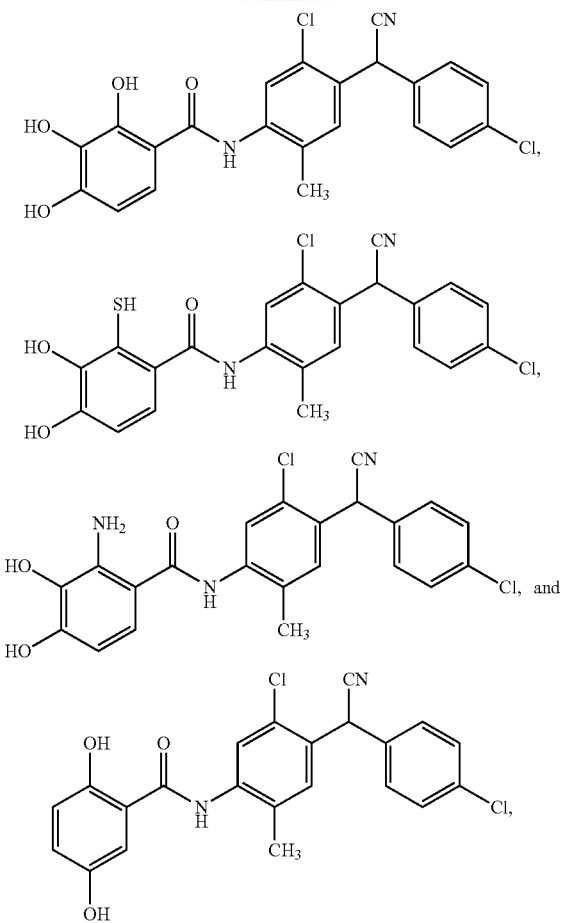

or a pharmaceutically acceptable salt thereof.

In one aspect, a compound can be selected from:

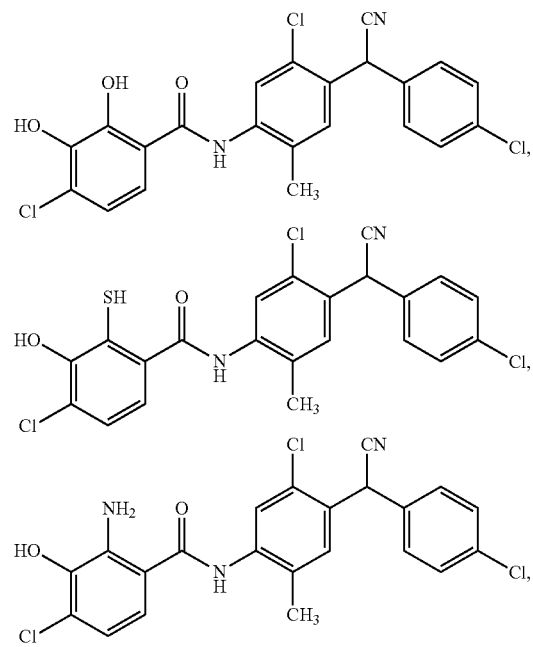

-continued

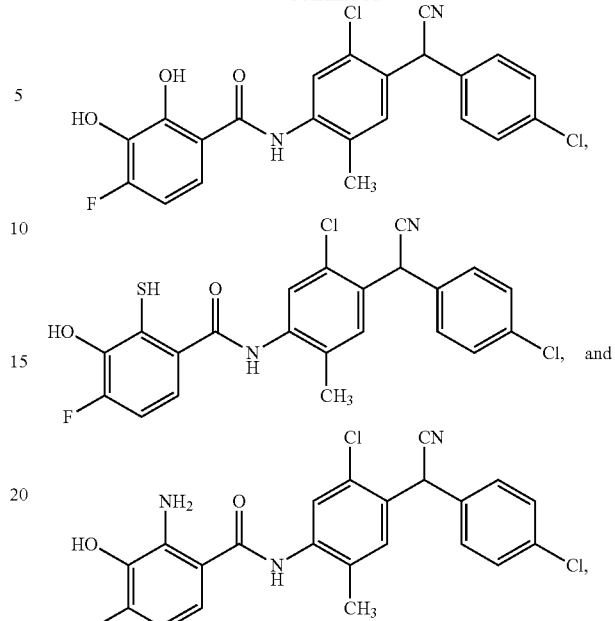

or a pharmaceutically acceptable salt thereof.

C. PHARMACEUTICAL COMPOSITIONS

In one aspect, disclosed are pharmaceutical compositions comprising a therapeutically effective of a disclosed compound, a pharmaceutically acceptable carrier, and one or more selected from: (a) at least one agent associated with the treatment of a neurodegenerative disease (e.g., amantadine, apomorphine, baclofen, carbidopa, carbidopa/levodopa, dantrolene, donepiezil, entacapone, galantamine, levodopa, memantine, pramipexole, rasagiline, riluzole, rivastigmine, ropinirole, selegiline, tacrine, tetrabenazine, tizanidine, tolcapone); (b) at least one agent associated with the treatment of a neurocognitive disease (e.g., cholinesterase inhibitors, memantine).

In various aspects, the compound has a structure represented by a formula:

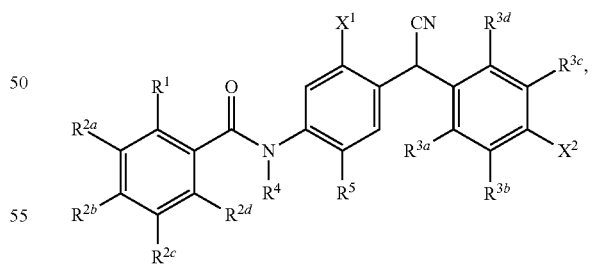

wherein each of $X^1$ and $X^2$ is independently halogen; wherein $R^1$ is selected from —OH, —$SR^{10}$, and —$NR^{11a}R^{11b}$; wherein each of $R^{10}$, $R^{11a}$, and $R^{11b}$, when present, is independently selected from hydrogen and C1-C4 alkyl; wherein each of $R^{2a}$, $R^{2b}$, $R^{2c}$, and $R^{2d}$ is independently selected from hydrogen, halogen, —$NO_2$, —CN, —OH, —SH, —$NH_2$, C1-C4 alkyl, C1-C4 haloalkyl, C1-C4 cyanoalkyl, C1-C2 hydroxyalkyl, C1-C4 alkoxy, C1-C4 thioalkyl, C1-C4 aminoalkyl, C1-C4 alkylamino, and (C1-

C4)(C1-C4) dialkylamino; wherein each of $R^{3a}$, $R^{3b}$, $R^{3c}$, and $R^{3d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino; wherein $R^4$ is selected from hydrogen and C1-C4 alkyl; and wherein $R^5$ is C1-C4 alkyl, provided that the compound is not:

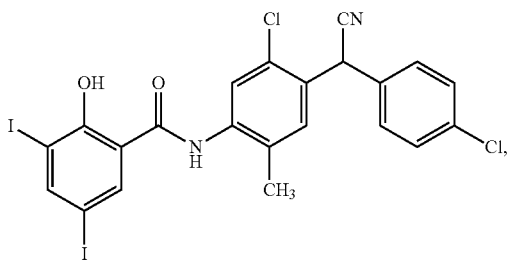

or a pharmaceutically acceptable salt thereof.

In various aspects, the compound is selected from:

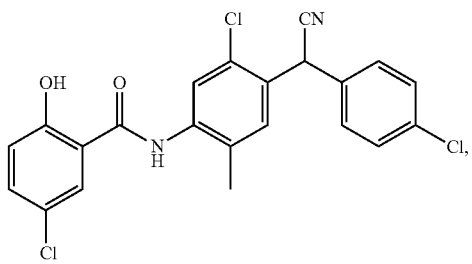

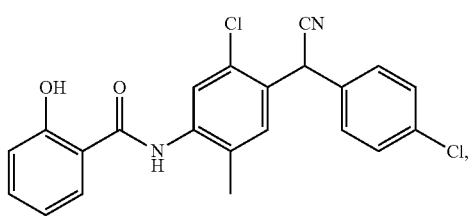

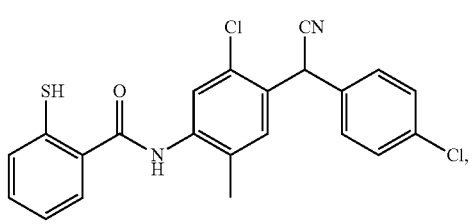

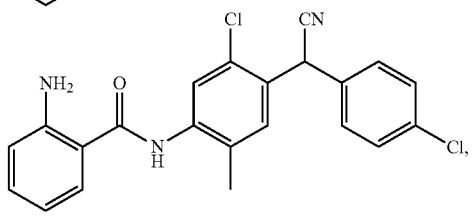

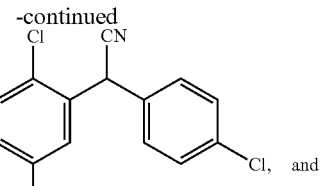

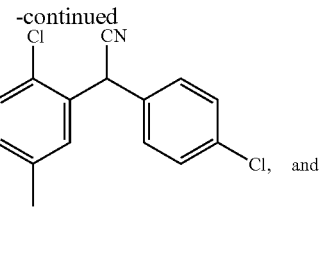

or a pharmaceutically acceptable salt thereof.

In various aspects, the compound is:

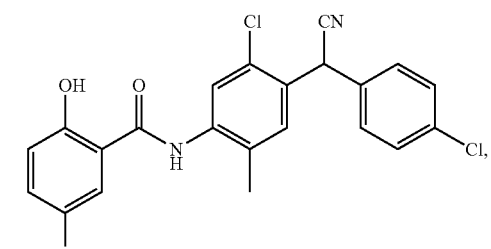

or a pharmaceutically acceptable salt thereof.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion;

gels or powders can be made for ingestion or topical application. Methods for making such formulations are well known and can be found in, for example, Remington's Pharmaceutical Sciences, 18th Ed., Gennaro, ed., Mack Publishing Co., Easton, Pa. 1990.

In various aspects, the disclosed pharmaceutical compositions comprise a disclosed compound (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, the effective amount is a therapeutically effective amount. In a still further aspect, the effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a neurodegenerative disease such as, for example, Alzheimer's disease, cerebral autosomal dominant arteriopathy with sub-cortical infarcts and leukoencephalopathy (CADASIL), Parkinson's disease, Huntington's disease, amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia, and Lewy body disease, or a neurocognitive disease such as, for example, dementia (e.g., vascular dementia, frontotemporal dementia, Lewy body dementia, mixed dementia, dementia induced by Alzheimer's disease or Parkinson's disease).

It is understood that the disclosed compositions can be prepared from the disclosed compounds. It is also understood that the disclosed compositions can be employed in the disclosed methods of using.

D. METHODS OF MAKING THE COMPOUNDS

In various aspects, the inventions relates to methods of making substituted N-(5-chloro-4-((4-chlorophenyl)(cyano)methyl)-2-methylphenyl)benzamide compounds useful in the treatment and/or prevention of neurodegenerative or neurocognitive disorders including, but not limited to, Alzheimer's disease, cerebral autosomal dominant arteriopathy with sub-cortical infarcts and leukoencephalopathy (CADASIL), Parkinson's disease, Huntington's disease, amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia, Lewy body disease, and dementia (e.g., vascular dementia, Lewy body dementia, frontotemporal dementia, mixed dementia, dementia induced by Alzheimer's disease or Parkinson's disease). Thus, in one aspect, disclosed are methods of making a disclosed compound.

Compounds according to the present disclosure can, for example, be prepared by the several methods outlined below. A practitioner skilled in the art will understand the appropriate use of protecting groups [see: Greene and Wuts, Protective Groups in Organic Synthesis] and the preparation of known compounds found in the literature using the standard methods of organic synthesis. There may come from time to time the need to rearrange the order of the recommended synthetic steps; however, this will be apparent to the judgment of a chemist skilled in the art of organic synthesis. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

1. Route I

In one aspect, substituted N-(5-chloro-4-((4-chlorophenyl)(cyano)methyl)-2-methylphenyl)benzamide compounds can be prepared as shown below.

SCHEME 1A.

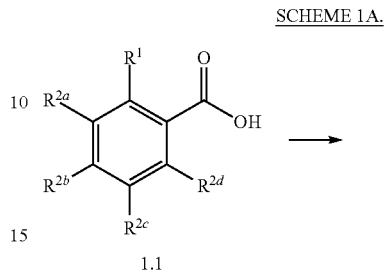

1.1

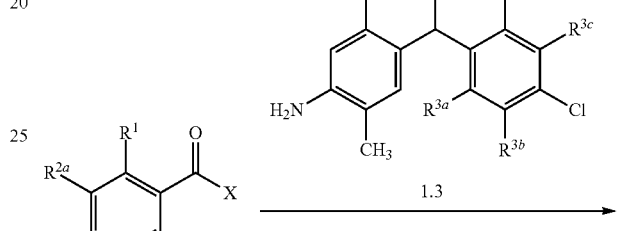

1.2

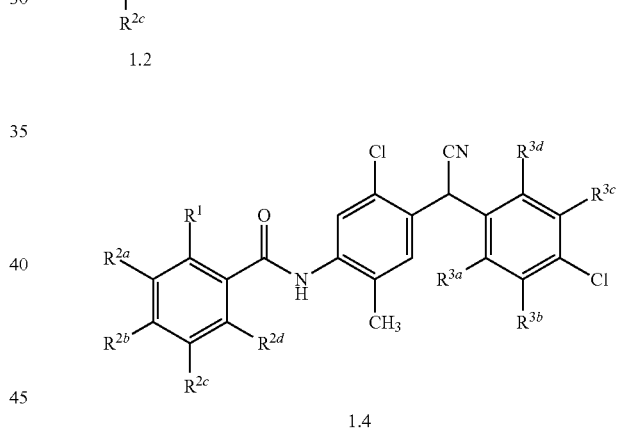

1.4

Compounds are represented in generic form, with substituents as noted in compound descriptions elsewhere herein and wherein X is a halogen. A more specific example is set forth below.

SCHEME 1B.

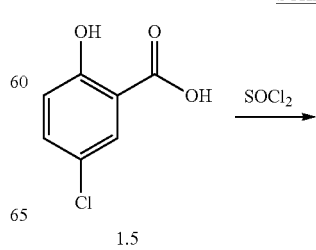

1.5

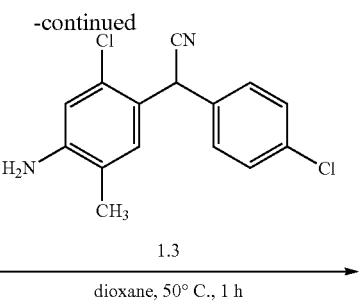

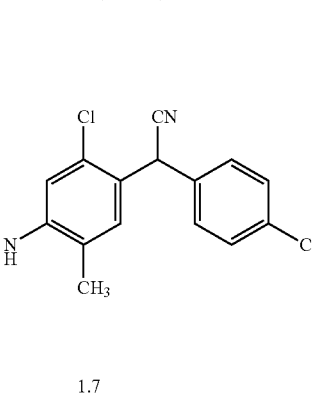

In one aspect, compounds of type 1.7, and similar compounds, can be prepared according to reaction Scheme 1B above. Thus, compounds of type 1.6 can be prepared by a nucleophilic substitution reaction of an appropriate carboxylic acid, e.g., 1.5 as shown above, and an appropriate activating agent, e.g., thionyl chloride as shown above. Appropriate carboxylic acids and appropriate activating agents are commercially available or prepared by methods known to one skilled in the art. Compounds of type 1.7 can be prepared by a coupling reaction between an appropriate activated carbonyl compound, e.g., 1.6 as shown above, and an appropriate amine, e.g., 1.3 as shown above. Appropriate amines are commercially available or prepared by methods known to one skilled in the art. The coupling reaction is carried out in the presence of an appropriate solvent, e.g., dioxane, for an appropriate period of time, e.g., 1 hour, at an appropriate temperature, e.g., 50° C. As can be appreciated by one skilled in the art, the above reaction provides an example of a generalized approach wherein compounds similar in structure to the specific reactants above (compounds similar to compounds of type 1.1, 1.2, and 1.3), can be substituted in the reaction to provide substituted N-(5-chloro-4-((4-chlorophenyl)(cyano)methyl)-2-methylphenyl)benzamide compounds similar to Formula 1.4.

E. METHODS OF USING THE COMPOUNDS

The compounds and pharmaceutical compositions of the invention are useful in treating or controlling conditions or disorders associated with a dysregulation of SPAK kinase function including, but not limited to, hypoxic brain injuries due to, for example, traumatic brain injury, ischemic stroke, carbon monoxide poisoning, drowning, choking, suffocating, or cardiac arrest. In a further aspect, the hypoxic brain injury is due to ischemic stroke or traumatic brain injury. In a still further aspect, the hypoxic brain injury is due to ischemic stroke.

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a cancer, immune dysfunction, or of a fibrotic disorder.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a hypoxic brain injury.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating and/or preventing neurodegenerative or neurocognitive disorders, but not limited to, Alzheimer's disease, cerebral autosomal dominant arteriopathy with sub-cortical infarcts and leukoencephalopathy (CADASIL), Parkinson's disease, Huntington's disease, amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia, Lewy body disease, and dementia (e.g., vascular dementia, Lewy body dementia, frontotemporal dementia, mixed dementia, dementia induced by Alzheimer's disease or Parkinson's disease). Thus, provided is a method comprising administering an effective amount of disclosed compound or a composition comprising a disclosed compound to a subject. In a further aspect, the method can be a method for treating or preventing dementia.

a. Treating and/or Preventing a Neurodegenerative Disease or a Neurocognitive Disease In one aspect, disclosed are methods of treating and/or preventing a neurodegenerative disease or a neurocognitive disease in a mammal, the method comprising the step of administering to the mammal an effective amount of at least one disclosed compound, or a pharmaceutically acceptable salt thereof.

Thus, in one aspect, disclosed are methods for treating and/or preventing a neurodegenerative disease or a neurocognitive disease in a subject in need thereof, the method comprising administering to the subject an effective amount of a compound having a structure represented by a compound having a structure represented by a formula:

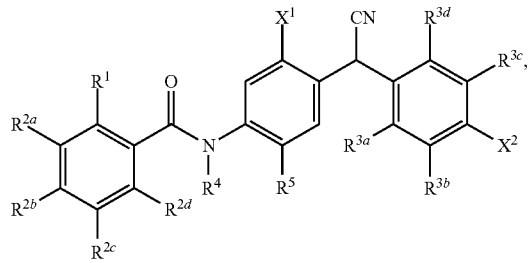

wherein each of $X^1$ and $X^2$ is independently halogen; wherein $R^1$ is selected from —OH, —$SR^{10}$, and —$NR^{11a}R^{11b}$; wherein each of $R^{10}$, $R^{11a}$, and $R^{11b}$, when present, is independently selected from hydrogen and C1-C4 alkyl; wherein each of $R^{2a}$, $R^{2b}$, $R^{2c}$, and $R^{2d}$ is independently selected from hydrogen, halogen, —$NO_2$, —CN, —OH, —SH, —$NH_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino; wherein each of $R^{3a}$, $R^{3b}$, $R^{3c}$, and $R^{3d}$ is independently selected from hydrogen, halogen, —$NO_2$, —CN, —OH, —SH, —$NH_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino; wherein $R^4$ is selected from hydrogen and C1-C4 alkyl; and wherein $R^5$ is C1-C4 alkyl, provided that the compound is not:

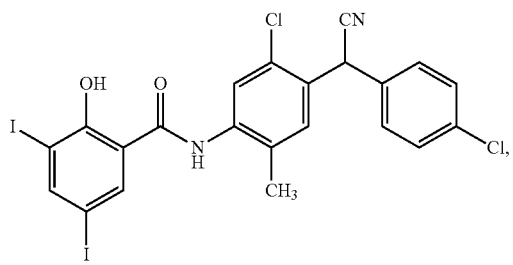 [SMILES: Cc1cc(C(C#N)c2ccc(Cl)cc2)c(Cl)cc1NC(=O)c1cc(I)cc(I)c1O]

or a pharmaceutically acceptable salt thereof.

In one aspect, disclosed are methods of treating and/or preventing dementia in a subject in in need thereof, the method comprising administering to the subject an effective amount of a compound having a structure represented by a formula:

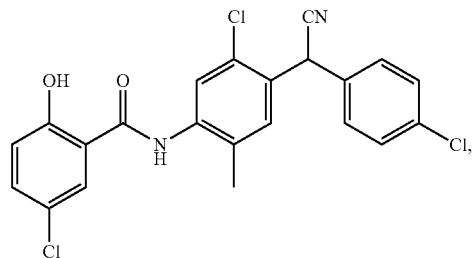 [SMILES: Cc1cc(C(C#N)c2ccc(Cl)cc2)c(Cl)cc1NC(=O)c1cc(Cl)ccc1O]

or a pharmaceutically acceptable salt thereof.

In a further aspect, the compound has a structure represented by a formula:

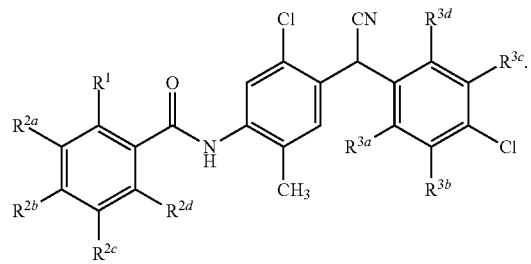

In various aspects, the method does not comprise administering an inhibitor of COX-1, COX-2, or lipoxygenase to the subject.

In a further aspect, the subject has been diagnosed with a need for treatment of a neurodegenerative or neurocognitive disease prior to the administering step. In a still further aspect, the subject has been diagnosed with a need for treatment of a neurodegenerative disease prior to the administering step. In yet a further aspect, the subject has been diagnosed with a need for treatment of a neurocognitive disease prior to the administering step.

In a further aspect, the subject is a mammal. In a still further aspect, the mammal is a human.

In a further aspect, the effective amount is a therapeutically effective amount. In a still further aspect, the effective amount is a prophylactically effective amount.

In a further aspect, the method further comprises the step of identifying a subject in need of treatment of a neurodegenerative or neurocognitive disease. In a still further aspect, the method further comprises the step of identifying a subject in need of treatment of a neurodegenerative disease. In yet a further aspect, the step of identifying a subject in need of treatment of a neurodegenerative In a further aspect, the subject has not previously been diagnosed as having had an ischemic stroke.

In a further aspect, the neurodegenerative or neurocognitive disease is associated with dysregulation of SPAK kinase.

In a further aspect, the method treats a neurodegenerative disease. In a still further aspect, the method prevents a neurodegenerative disease. Examples of neurodegenerative diseases include, but are not limited to, Alzheimer's disease, cerebral autosomal dominant arteriopathy with sub-cortical infarcts and leukoencephalopathy (CADASIL), Parkinson's disease, Huntington's disease, amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia, and Lewy body disease.

In a further aspect, the method treats a neurocognitive disease. In a still further aspect, the method prevents a neurocognitive disease. Examples of neurocognitive diseases include dementia such as, for example, vascular dementia, frontotemporal dementia, Lewy body dementia, mixed dementia, and dementia induced by Alzheimer's disease or Parkinson's disease.

In a further aspect, the method further comprises the step of administering a therapeutically effective amount of at least one agent associated with the treatment of a neurodegenerative disease. Examples of agents associated with the treatment of neurodegenerative disease include, but are not limited to, amantadine, apomorphine, baclofen, carbidopa, carbidopa/levodopa, dantrolene, donepiezil, entacapone, galantamine, levodopa, memantine, pramipexole, rasagiline, riluzole, rivastigmine, ropinirole, selegiline, tacrine, tetrabenazine, tizanidine, and tolcapone.

In a further aspect, the at least one compound and the at least one agent associated with the treatment of a neurodegenerative disease are administered sequentially. In a still further aspect, the at least one compound and the at least one agent associated with the treatment of a neurodegenerative disease are administered simultaneously.

In a further aspect, the at least one compound and the at least one agent associated with the treatment of a neurodegenerative disease are co-formulated. In a still further aspect, the at least one compound and the at least one agent associated with the treatment of a neurodegenerative disease are co-packaged.

In a further aspect, the method further comprises the step of administering a therapeutically effective amount of at least one agent associated with the treatment of a neurocognitive disease. Examples of agents associated with the treatment of neurocognitive disease include, but are not limited to, cholinesterase inhibitors and memantine.

In a further aspect, the at least one compound and the at least one agent associated with the treatment of a neurocognitive disease are administered sequentially. In a still further aspect, the at least one compound and the at least one agent associated with the treatment of a neurocognitive disease are administered simultaneously.

In a further aspect, the at least one compound and the at least one agent associated with the treatment of a neurocognitive disease are co-formulated. In a still further aspect, the at least one compound and the at least one agent associated with the treatment of a neurocognitive disease are co-packaged.

2. Use of Compounds

In one aspect, the invention relates to the use of a disclosed compound or a product of a disclosed method. In a further aspect, a use relates to the manufacture of a medicament for the treatment and/or prevention of a neurodegenerative or a neurocognitive disease in a mammal.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder or condition in a mammal. Also disclosed is the use of a compound for modification of SPAK kinase function. In one aspect, the use is characterized in that the mammal is a human. In one aspect, the use is characterized in that the disorder or condition is a neurodegenerative disease. In one aspect, the use is characterized in that the disorder or condition is a neurocognitive disease such as, for example, dementia.

In a further aspect, the use relates to the manufacture of a medicament for the treatment and/or prevention of a neurodegenerative or neurocognitive disease in a mammal.

In a further aspect, the use relates to modulation of SPAK kinase function in a mammal. In a further aspect, the use relates to inhibition of SPAK kinase function in a mammal. In a still further aspect, the use relates to modulation of SPAK kinase function in a cell. In yet a further aspect, the mammal is a human.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment and/or prevention of a neurodegenerative disease in a mammal. In a further aspect, the invention relates to the use of a disclosed compound or a disclosed product in the manufacture of a medicament for the treatment and/or prevention of a neurocognitive disease in a mammal such as, for example, dementia.

3. Manufacture of a Medicament

In one aspect, the invention relates to a method for the manufacture of a medicament for treating and/or preventing a neurodegenerative or neurocognitive disorder in a mammal, the method comprising combining an effective amount (for example, a therapeutically effective amount) of a disclosed compound or product of a disclosed method with a pharmaceutically acceptable carrier or diluent.

As regards these applications, the present method includes the administration to an animal, particularly a mammal, and more particularly a human, of an effective amount of the compound effective in treating/preventing neurodegenerative and neurocognitive diseases. The dose administered to an animal, particularly a human, in the context of the present invention should be sufficient to affect an effective response (e.g., a therapeutically effective response or a prophylactically effective response) in the animal over a reasonable timeframe. One skilled in the art will recognize that dosage will depend upon a variety of factors including, for example, the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

4. Kits

In one aspect, disclosed are kits comprising a compound having a structure represented by a compound having a structure represented by a formula:

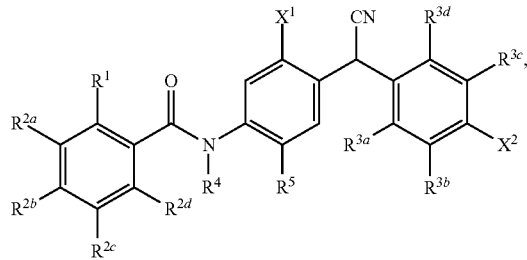

wherein each of $X^1$ and $X^2$ is independently halogen; wherein $R^1$ is selected from —OH, —SR$^{10}$, and —NR$^{11a}$R$^{11b}$; wherein each of $R^{10}$, $R^{11a}$, and $R^{11b}$, when present, is independently selected from hydrogen and C1-C4 alkyl; wherein each of $R^{2a}$, $R^{2b}$, $R^{2c}$, and $R^{2d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino; wherein each of $R^{3a}$, $R^{3b}$, $R^{3c}$, and $R^{3d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino; wherein $R^4$ is selected from hydrogen and C1-C4 alkyl; and wherein $R^5$ is C1-C4 alkyl, provided that the compound is not:

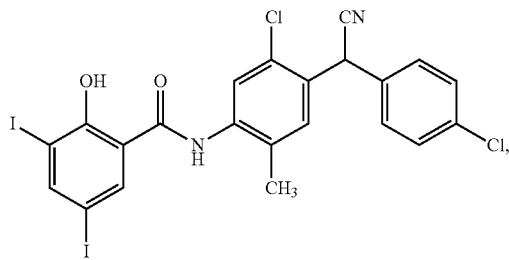 [SMILES: Cc1cc(C(C#N)c2ccc(Cl)cc2)c(Cl)cc1NC(=O)c1cc(I)cc(I)c1O]

or a pharmaceutically acceptable salt thereof, and one or more of: (a) at least one agent associated with the treatment of a neurodegenerative disease; (b) at least one agent associated with the treatment of a neurocognitive disease; (c) instructions for administering the compound in connection with treating a neurodegenerative disease; (d) instructions for administering the compound in connection with treating a neurocognitive disease; (e) instructions for treating a neurodegenerative disease; and (f) instructions for treating a neurocognitive disease.

In a further aspect, the compound has a structure represented by a formula:

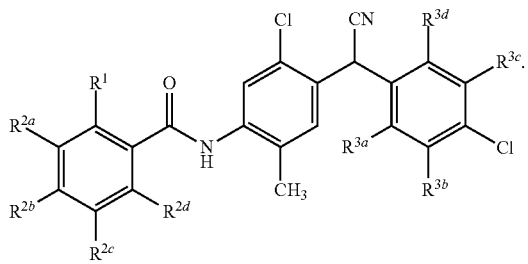

Examples of agents associated with the treatment of a neurodegenerative disease include, but are not limited to, amantadine, apomorphine, baclofen, carbidopa, carbidopa/levodopa, dantrolene, donepiezil, entacapone, galantamine, levodopa, memantine, pramipexole, rasagiline, riluzole, rivastigmine, ropinirole, selegiline, tacrine, tetrabenazine, tizanidine, and tolcapone. Thus, in a further aspect, the agent associated with the treatment of a neurodegenerative disease is selected from amantadine, apomorphine, baclofen, carbidopa, carbidopa/levodopa, dantrolene, donepiezil, entacapone, galantamine, levodopa, memantine, pramipexole, rasagiline, riluzole, rivastigmine, ropinirole, selegiline, tacrine, tetrabenazine, tizanidine, and tolcapone.

In a further aspect, the at least one compound and the at least one agent associated with the treatment of a neurodegenerative disease are co-formulated. In a further aspect, the at least one compound and the at least one agent associated with the treatment of a neurodegenerative disease are co-packaged.

Examples of agents associated with the treatment of a neurocognitive disease include, but are not limited to, cholinesterase inhibitors and memantine. Thus, in a further aspect, the agent associated with the treatment of a neurocognitive disease is selected from a cholinesterase inhibitor and memantine.

In a further aspect, the at least one compound and the at least one agent associated with the treatment of a neurocognitive disease are co-formulated. In a further aspect, the at least one compound and the at least one agent associated with the treatment of a neurocognitive disease are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

F. EXAMPLES

The following preparations and examples are given to enable those skilled in the art to more clearly understand and to practice the present invention. They should not be considered as limiting the scope of the invention, but merely as being illustrative and representative.

Figure 1A:
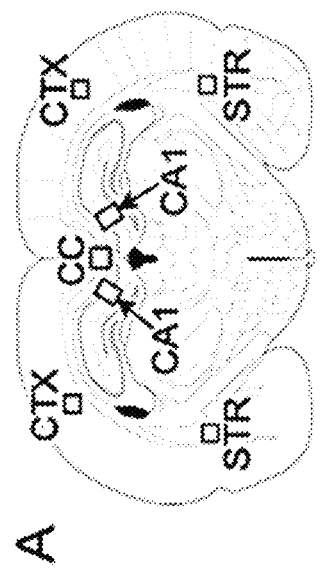
Figure 1C:
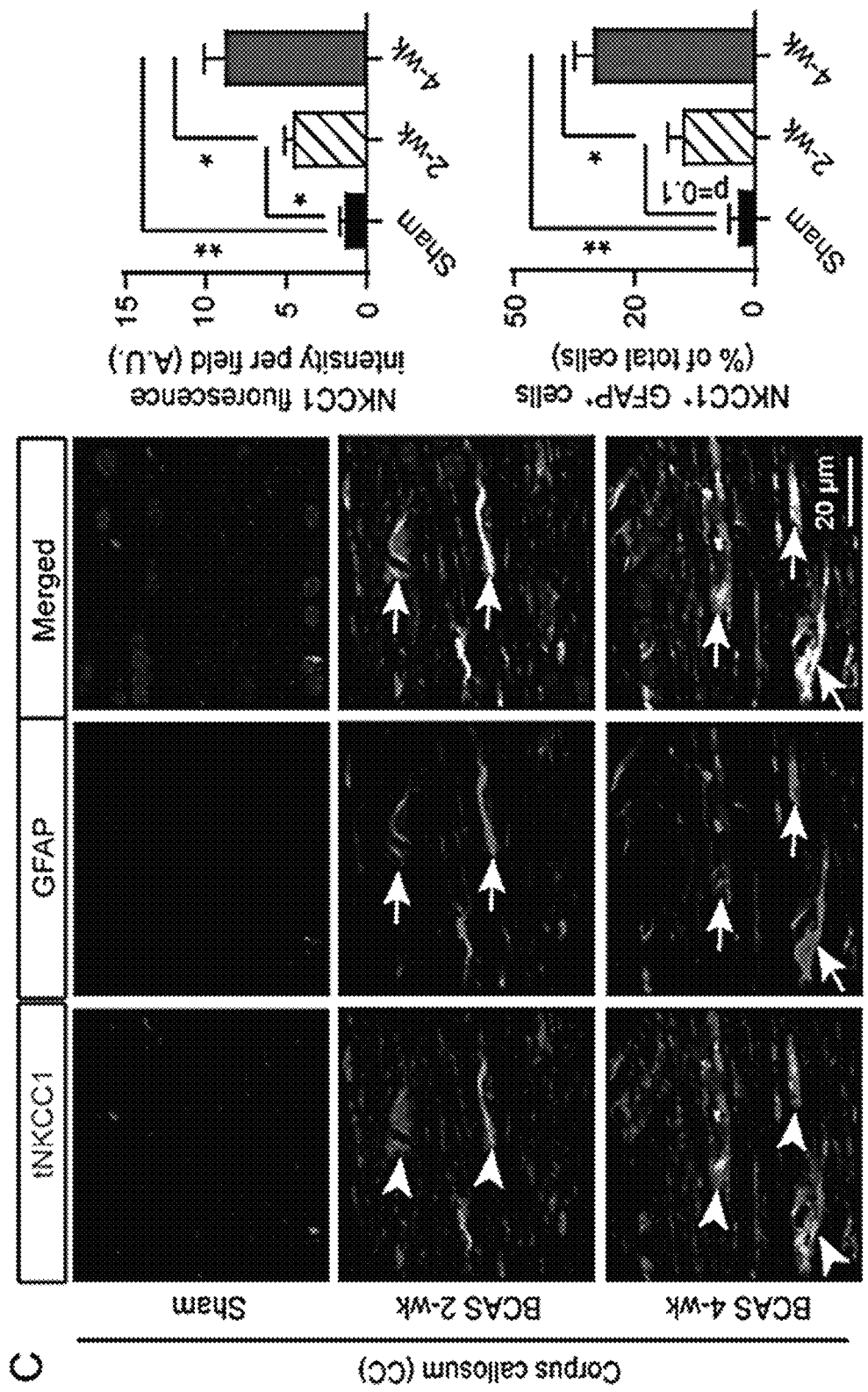
Figure 1D:
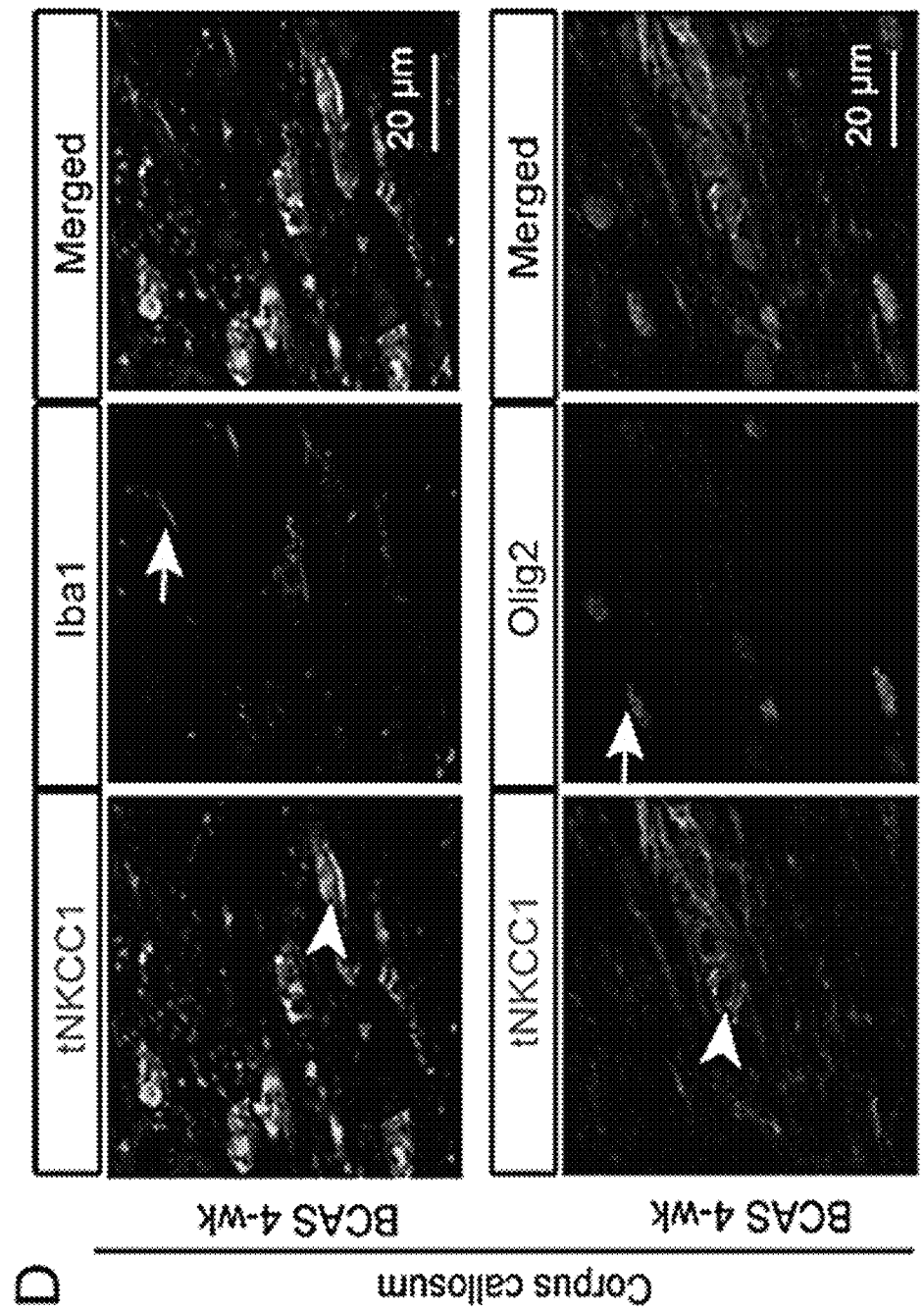

1. BCAS-Induced Early Upregulation of NKCC1 Protein in White Matter GFAP$^+$ Reactive Astrocytes Clinically, most patients with intracranial atherosclerotic stenosis suffer from permanent stenosis without occlusion. Therefore, to mimic clinical atherosclerotic stenosis with permanent carotid artery (CCA) hypoperfusion, a modified BCAS model was adapted by ligating the CCA guided with a 30 gauge needle (0.31 mm diameter) in the right CCA and a 33 gauge needle (0.21 mm diameter) in the left CCA with a 4-0 silk suture. Comparing to Sham-controls, the modified BCAS procedures in adult C57BL/6J mice (male, 2-4 months) led to initial reduction blood flow in both CCA (~25% in the right, and ~75% in the left) at the onset of the ligation surgery. However, over 2-6 wks post-surgery, they resulted in sustained cerebral hypoperfusion in both hemispheres. Next, changes of total NKCC1 (tNKCC1) protein expression were surveyed in different brain regions at 2 and 4 wks post-surgery by immunofluorescence staining (IF). As illustrated in FIG. 1A, compared to cortex (CTX), striatum (STR) and hippocampal CA1 regions at 4 wks post-surgery, BCAS triggered most robust increases of tNKCC1 proetin expression in reactive GFAP$^+$ astrocytes in the corpus collosum (CC) region (FIG. 1B). Therefore, in the rest of the study, the investigation was focused on its association to white matter GFAP$^+$ astrogliosis and lesion of CC and external capsul (EC) tracks. FIG. 1C shows that Sham-control CC displayed barely detectable level of tNKCC1 protein expression. However, by 2 wks post-BCAS surgery, tNKCC1 immunofluorescence intensity in the CC tracks was increased by ~3 folds (p<0.05), and further elevated to ~6 folds by 4 wks (p<0.05, arrowhead). Data are mean±SEM, n=4, *p<0.05, **p<0.01. Specifically, the upregulated tNKCC1 protein was located along the fiber track and especially enriched within the GFAP$^+$ reactive astrocytes (arrow). The upregulation of tNKCC1 and GFAP protein expression in the CC is correlated, with a Pearson's correlation coefficient of r=0.9 (p<0.001). Without wishing to be bound by theory, these data imply that pathological stimulation of NKCC1 protein may play a role in reactive GFAP$^+$ astrocyte activation and white matter lesion (WML) after BCAS. In contrast, no elevated tNKCC1 protein was detected either in Iba1$^+$ microglia/macrophages or in Olig2+ oligodendrocytes (OL) at 4 wks post-BCAS surgery (FIG. 1D). Without wishing to be bound by theory, these findings indicate that upregulation of NKCC1 expression and activity in reactive astrocytes may play a critical role in white matter inflammation, OL death, and demyelination after BCAS.

Referring to FIG. 1A, the brain section illustrates sample collection in the cortex (CTX), corpus callosum (CC), hippocampal CA1 subfield [stratum pyramidale (SP) and stratum radiatum (SR)], and striatum (STR) areas.

Figure 2A:
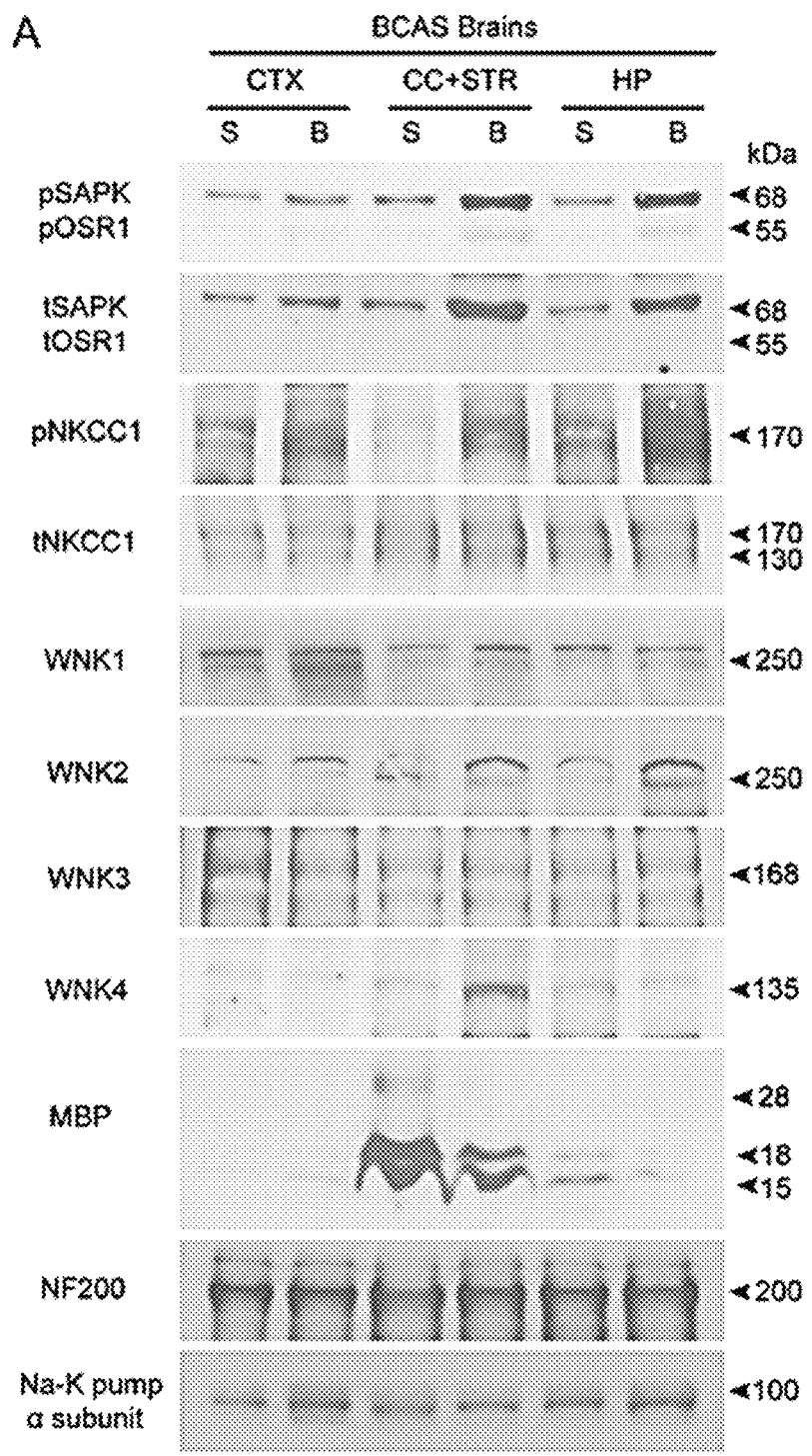
FIG. 2A-D show representative data illustrating WNK-SPAK-NKCC1 cascade protein stimulation after BCAS.

2. Validation of BCAS-Mediated Robust Activation of the WNK-SPAK-NKCC1 Signaling Complex Via Immunoblotting Using the following authenticated antibodies, including anti-pNKCC1 (pThr212), anti-pSPAK/OSR1 (pSer383 SPAK, pSer325 OSR1), anti-tNKCC1, tSPAK/tOSR1, tWNK1, tWNK2, tWNK3, or tWNK4 antibodies, changes of the WNK-SPAK/OSR1-NKCC1 signaling complex were quantified in different brain regions, cortex (CTX), CC-subcortical striatum (CC+STR), and hippocampus (HP), of Sham and BCAS mice (adult C57BL/6J). Compared to the Sham controls, BCAS triggered significant increases in pSPAK/pOSR1 (pSer383/pSer325) and pNKCC1 (pThr212) expression at 4 wks post-BCAS (p<0.05, FIG. 2A-C). Total tSPAK/tOSR1, tWNK1, tWNK2, tWNK4 were also significantly upregulated (p<0.05, FIG. 2B-D). Myelin basic protein (MBP) was enriched in the white matter region (CC-STR) of Sham control brains. Further, BCAS triggered a massive reduction of MBP expression while neurofilament heavy chain NF 200 expression was unchanged (FIG. 2A and FIG. 2D). Taken together, these data further validate that the WNK-SPAK-NKCC1 signaling pathway is robustly activated in the mouse brain after BCAS.

Referring to FIG. 2A, representative immunoblots of increased WNK-SPAK/OSR-1-NKCC1 complex proteins and decreased myeling basic protein (MBP) in BCAS-induced hypoperfused mouse brains (membrane protein fractions) at 4-wk after surgery. Na-K pump (α subunit) was used as loading control.

Figure 2B:
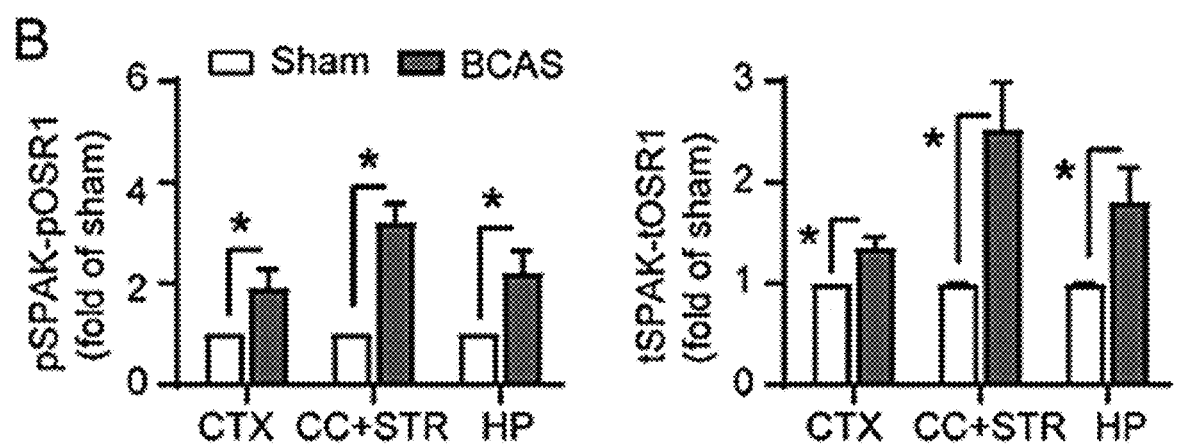
Figure 2C:
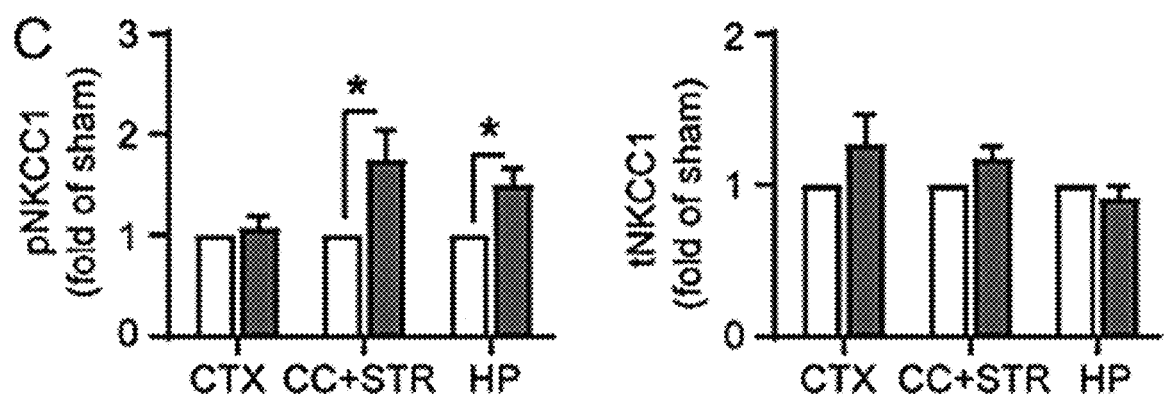
Figure 2D:
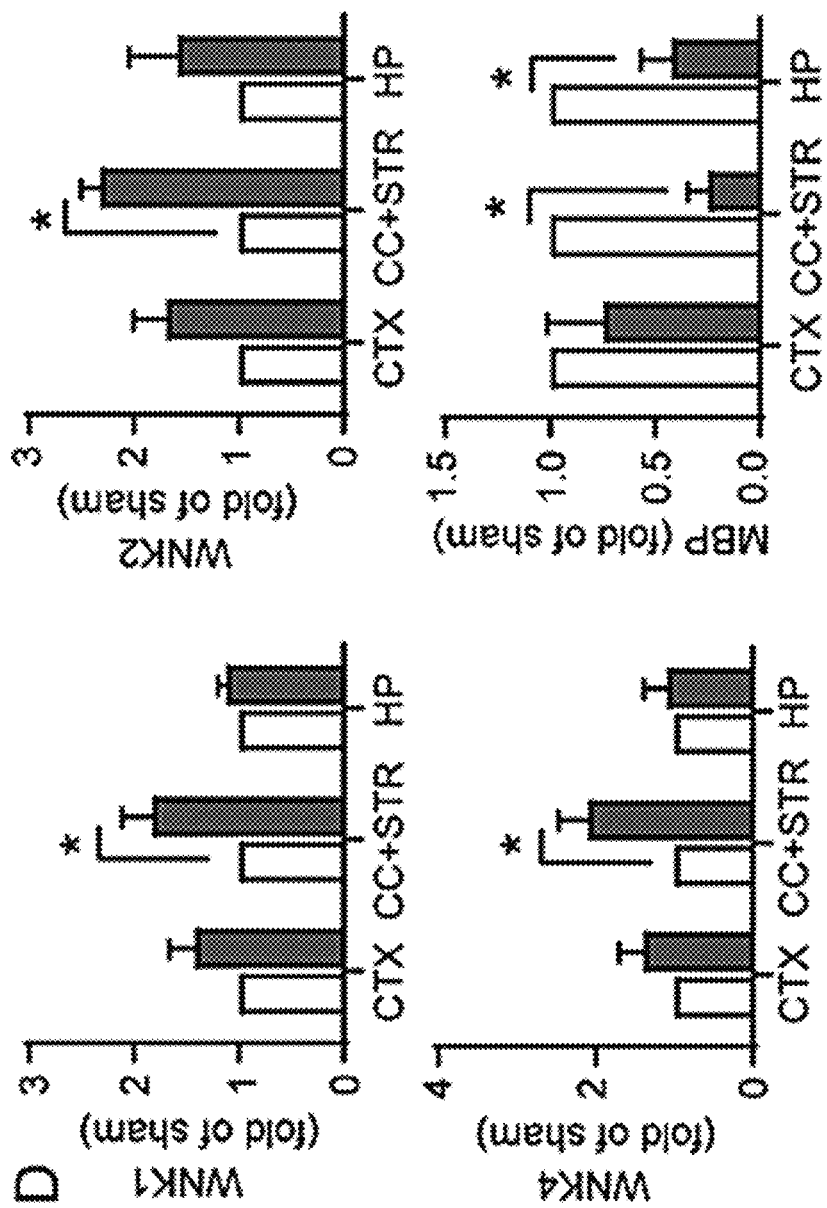

Referring to FIG. 2B-D, quantitative analyses are shown. Data are mean±SEM. N=4, *p<0.05. BCAS: bilateral carotid artery stenosis; CTX: cortex; CC: corpus callosum; STR: striatum; HP: hippocampus; S: sham; B: BCAS.

Figure 3A:
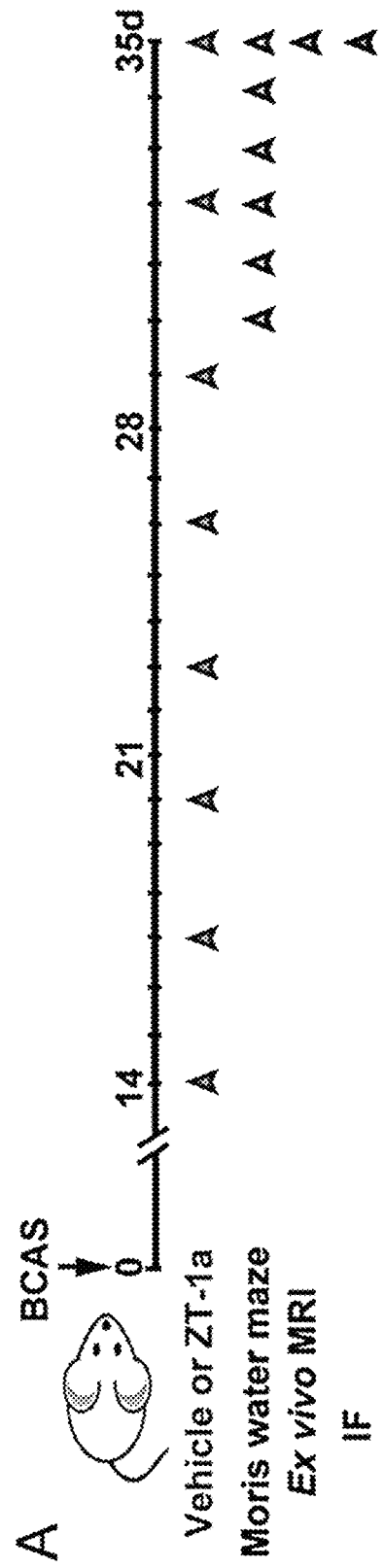
FIG. 3A and FIG. 3B show representative data illustrating that SPAK inhibition prevents learning and memory impairments after BCAS.
Figure 3B:
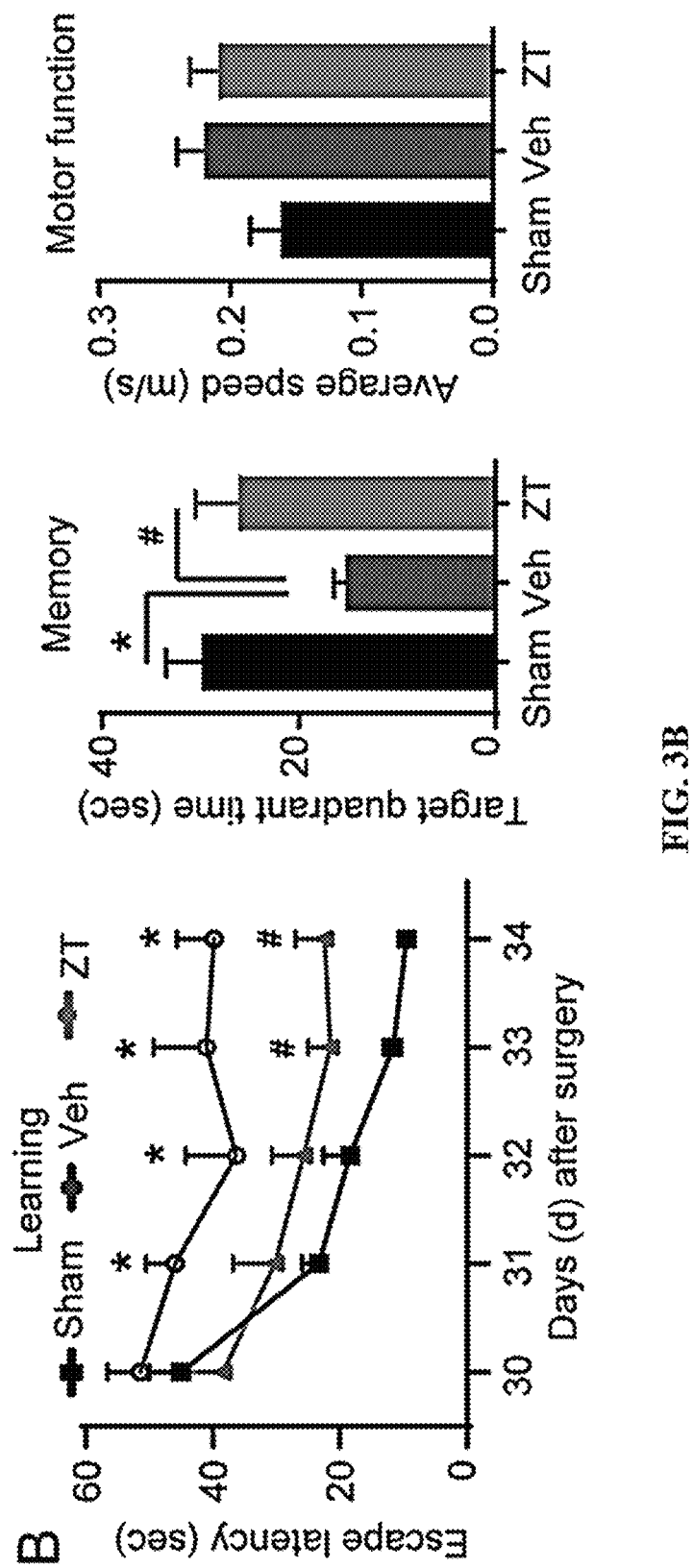

3. Administration of SPAK Inhibitor ZT-1a in C57BL/6J Mice at 2-4 Weeks Post-BCAS Reduces Cognitive Deficits Next, whether administration of SPAK inhibitor ZT-1a reduces WML and improves cognitive functions was examined. Starting at 14 days after BCAS surgery in mice (male), either vehicle DMSO (Veh, 2 ml/kg) or ZT-1a (5 mg/kg, every 72 h, i.p) was administered every 3 days, until they were sacrificed at day 35 post-BCAS (FIG. 3A). As shown in FIG. 3B, compared to Sham controls, the Veh-treated BCAS mice failed to show learning and memory (no significant changes in escape latency during 5-day MWM test) at 4 wks post-BCAS. In contrast, ZT-1a-treated BCAS mice displayed improved performance in learning with significantly less escape latency (FIG. 3B). Moreover, in the spatial probe trial, ZT-1a-treated mice spent significantly longer time in the target quadrant (26.3±4.3 sec) than the Veh-treated BCAS mice (15.3±1.2 sec, p<0.05), suggesting that ZT-1a-treated mice retained better spatial memory function (FIG. 3B). Motor functions are similar in all groups and average swimming speeds were not different in the Sham-, Veh- and ZT-1a-treated mice. Data are mean±SEM, n=6 (Sham and ZT-1a) or 5 (Veh), *p<0.01 vs. sham, *p<0.05 vs. Veh.

Figure 4A:
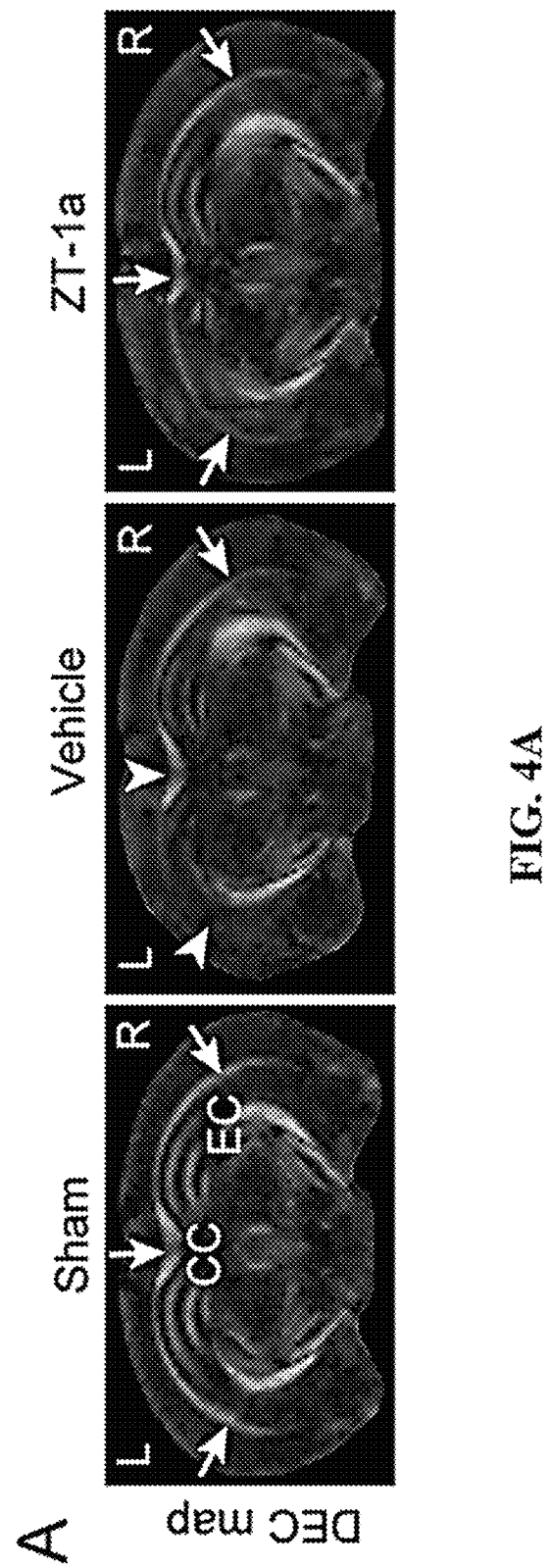
FIG. 4A-D show representative data illustrating that ZT-1a protects white matter disruption and myelin basic protein (MBP) loss following BCAS.
Figure 4B:
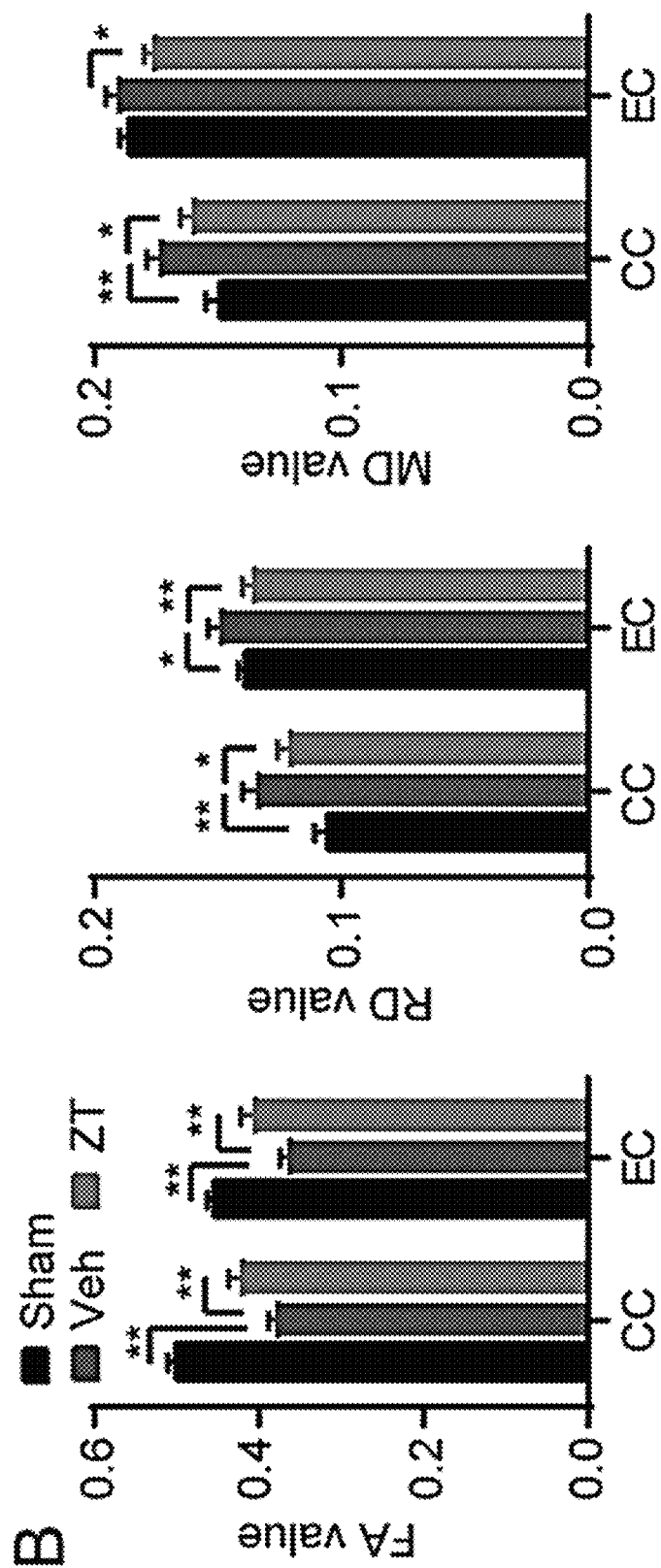
Figure 4C:
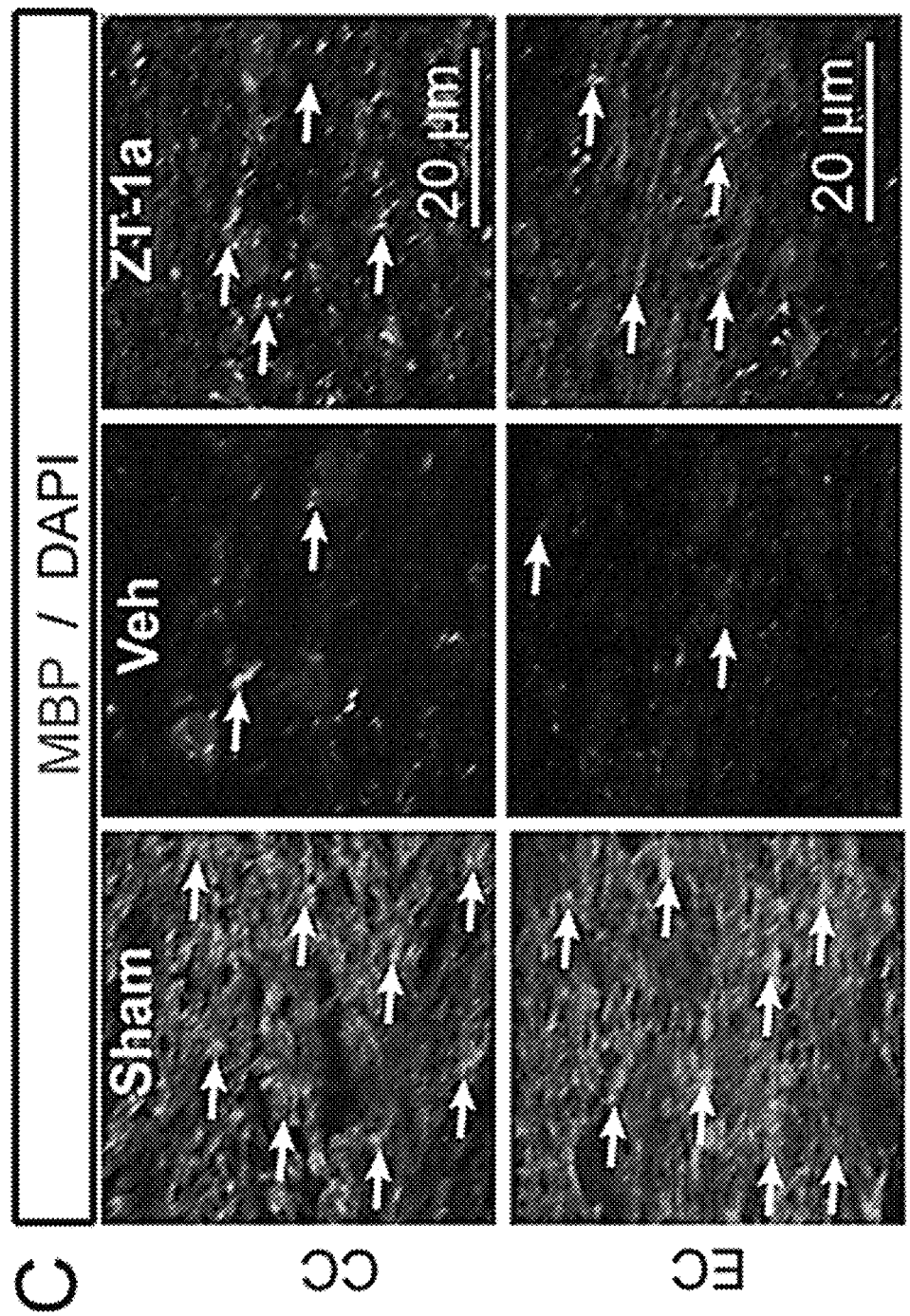

4. The SPAK Inhibitor ZT-1a-Treated BCASE Mice Displayed Improved White Matter Integrity After completion of the neurological function tests in the Veh-control and ZT-1a-treated BCAS cohort mice (as shown in FIG. 3A and FIG. 3B), ex-vivo brains were harvested for MRI DTI (diffusion tensor imaging) analysis of WML at 4 wks post-BCAS detected by DTI. The fractional anisotropy (FA), radial diffusivity (RD), and mean diffusivity (MD) of the CC and EC tracks were analyzed. Representative images of the DEC maps in FIG. 4A show severe loss of axonal fibers (arrowheads) in the CC and left EC of the Veh-control brains. In contrast, the ZT-1a-treated mice exhibited better-preserved integrity of the CC and EC tracks in both hemispheres (arrows). These observations are consistent with changes of FA, RD, and MD values (FIG. 4B). The Veh-control group showed significantly reduced FA values in the CC tract (0.383±0.004), compare to the Sham-controls (0.502±0.009, p<0.01). This is corroborated with increases in the Veh-control RD (0.135±0.004 vs 0.106±0.004) and MD (0.174±0.001 vs 0.149±0.005) values. In contrast, ZT-1a-treated mice displayed significantly higher FA values, and lower RD and MD values than that of the Veh-control groups (p<0.05), reflecting a preserved white matter microstructure. Then MBP expression levels were measured in these brains by immunostaining. FIG. 4C showed massive loss of MBP protein expression in the CC and EC tracks of the Veh-treated BCAS brains, compared to Sham controls. In contrast, the ZT-1a-treated brains exhibited less MBP loss (p<0.05, FIG. 4D). Taken together, these findings illustrated that post-BCAS administration of SPAK inhibitor ZT-1a reduces BCAS-induced white matter demyelination.

Referring to FIG. 4B, data are mean±SEM, n=7, *p<0.05, **p<0.01.

Figure 4D:
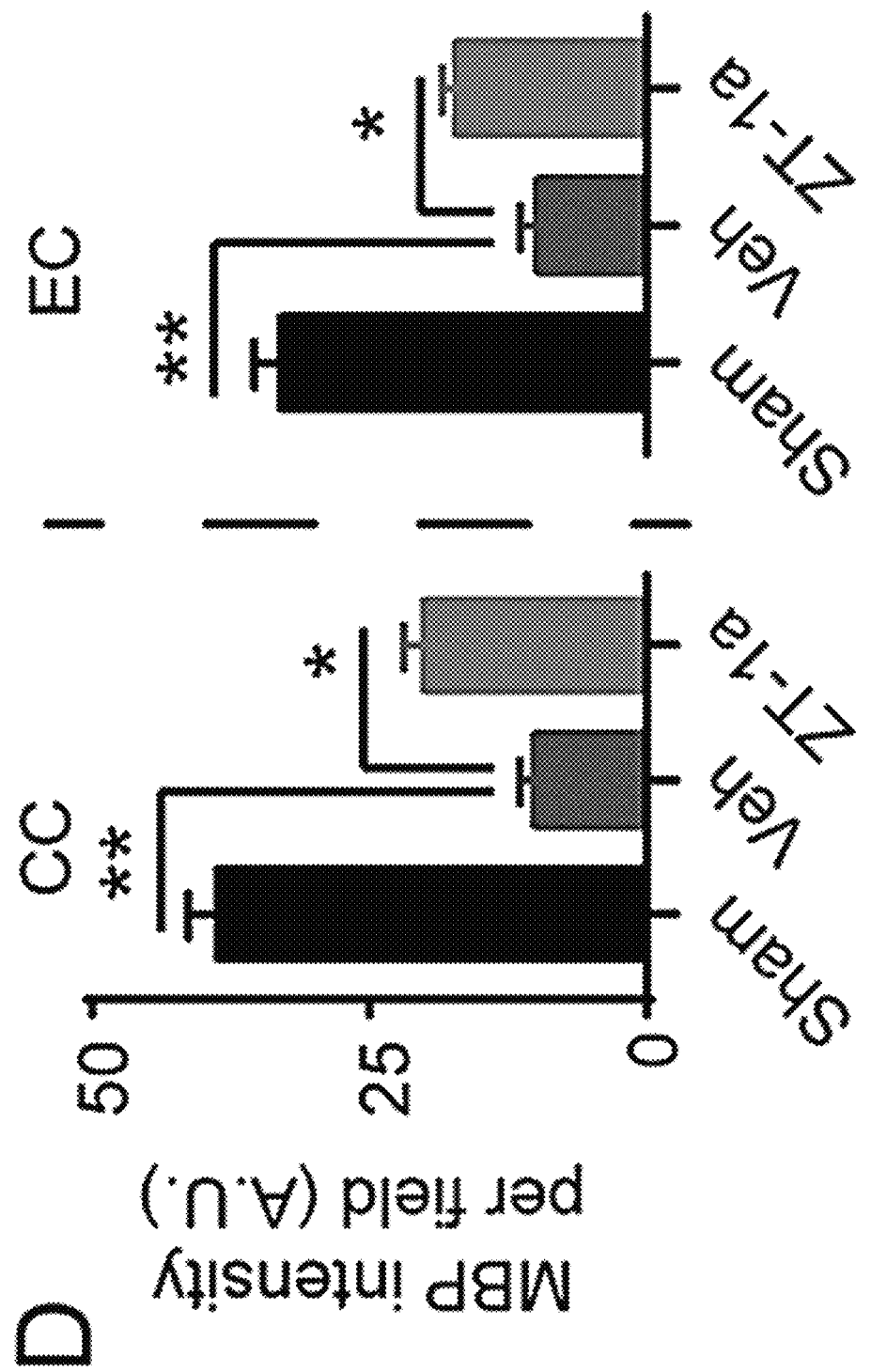

Referring to FIG. 4D, data are mean±SEM, n=4, *p<0.05, **p<0.01.

5. The SPAK Inhibitor ZT-1a-Treated BCAS Mice Displayed Reduced Loss of Oligodendrocytes (OLs)

Figure 5A:
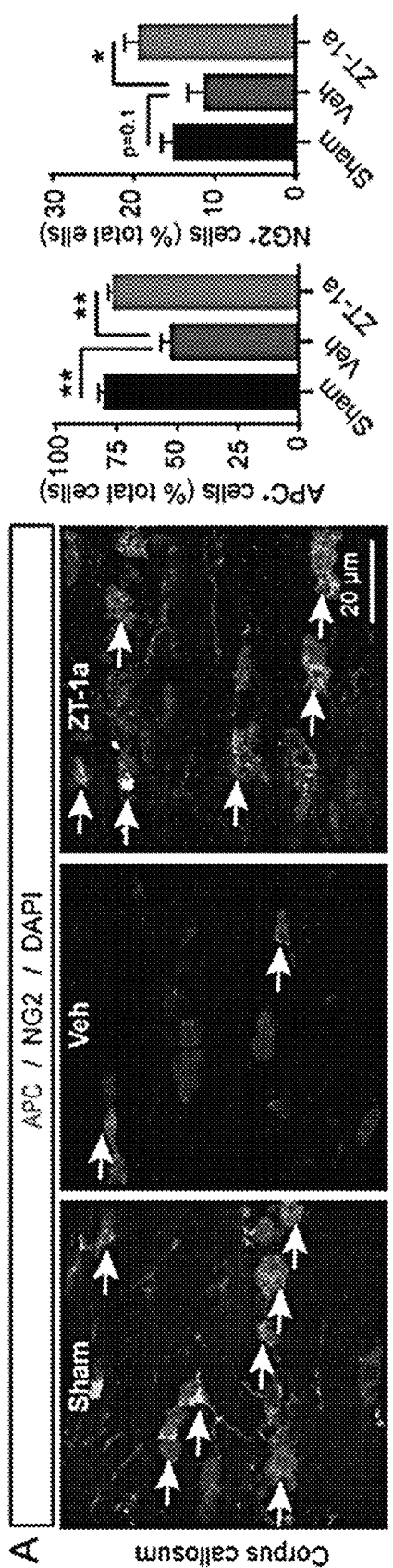
FIG. 5A-C show representative data illustrating that ZT-1a prevents BCAS-mediated loss of both oligodendrocyte precursor cells (OPCs) and oligodendrocytes (OLs) in corpus callosun (CC) and external capsul (EC) at 4 weeks after BCAS.
Figure 5B:
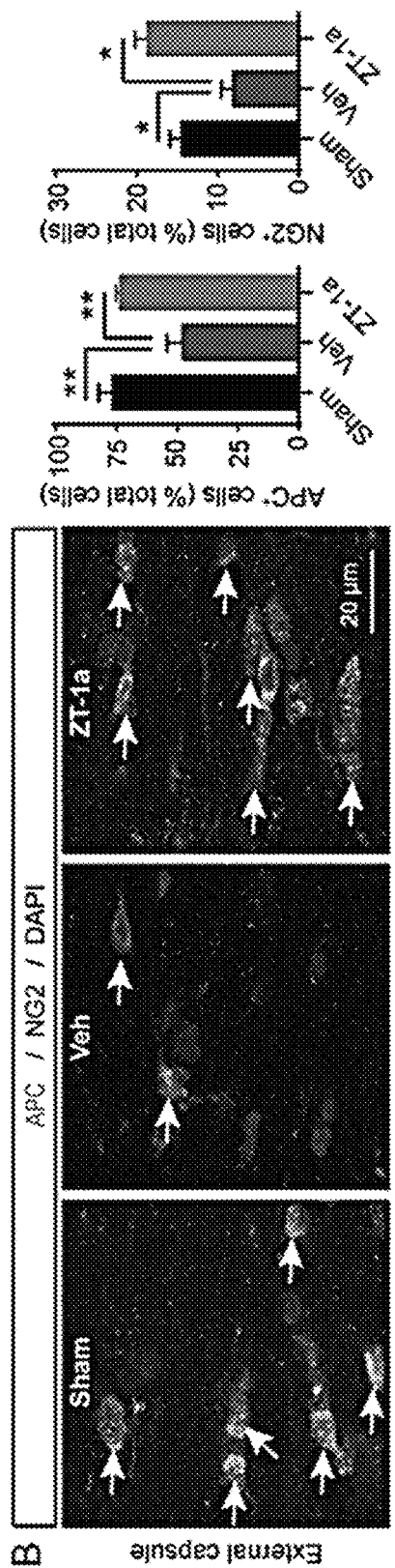
Figure 5C:
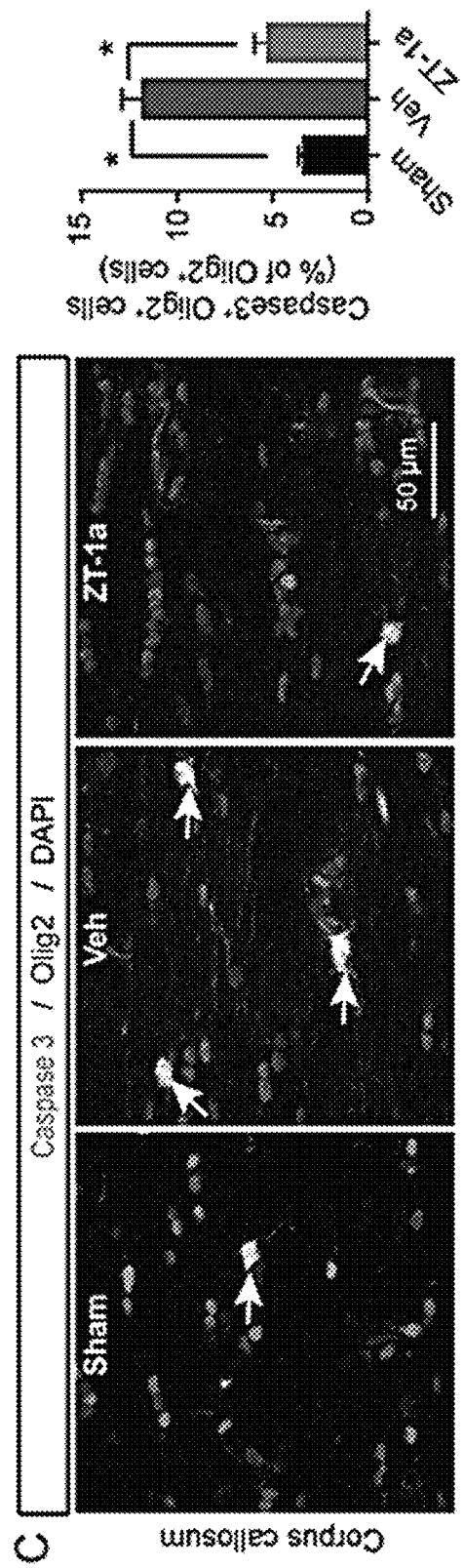

Whether better-preserved white matter integrity displayed in the ZT-1a-treated mice is due to increased oligodendrogenesis and/or decreased OLs cell death was examined next. To test this, immunostaining of the same cohort of brains (of FIG. 4A-D) was conducted to analyze oligodendrocyte precursor cell (OPC) counts (NG2$^+$), differentiated mature OLs (APC$^+$), and apoptotic OLs (caspase 3$^+$Olig2$^+$) in the Sham, Veh-, and ZT-1a-treated BCAS mice. As shown in FIG. 5A-C, compared to Sham mice, the Veh-treated BCAS mice exhibited significant loss of APC$^+$ mature OLs and NG2$^+$ OPC cells in the CC and EC tracks, and increased caspase 3$^+$ OLs cell counts in CC at 4 wks post-BCAS. In contrast, the ZT-1a-treated BCAS mice showed significantly higher APC$^+$ cell counts and NG2$^+$ cell counts in the CC and EC tracts, and less caspase 3$^+$ OLs cell counts in CC, compared to that of Veh-controls (FIG. 5A-C). Without wishing to be bound by theory, these data suggest that ZT-1a treatment prevented cell death of OPC and OLs and/or increased proliferation of OPCs.

Referring to FIG. 5A and FIG. 5B, representative double immunofluorescence images of APC (mature oligodendrocyte marker)/NG2 (oligodendrocyte precursor cell marker) in CC (FIG. 5A) and EC (FIG. 5B) of Sham, Veh-, and ZT-1a-treated brains at 4-wk after BCAS surgery. Nuclei were counterstained with DAPI. Quantitative analyses of APC$^+$/DAPI$^+$ cells and NG2$^+$/DAPI$^+$ cells is shown. Data are mean±SEM, n=4, *p<0.05, **p<0.05.

Referring to FIG. 5C, representative double immunofluorescence images of Caspase 3$^+$/Olig2$^+$ cells in CC of Sham, Veh-, and ZT-1a-treated brains. Data are mean±SEM, n=4, *p<0.05.

Figure 6:
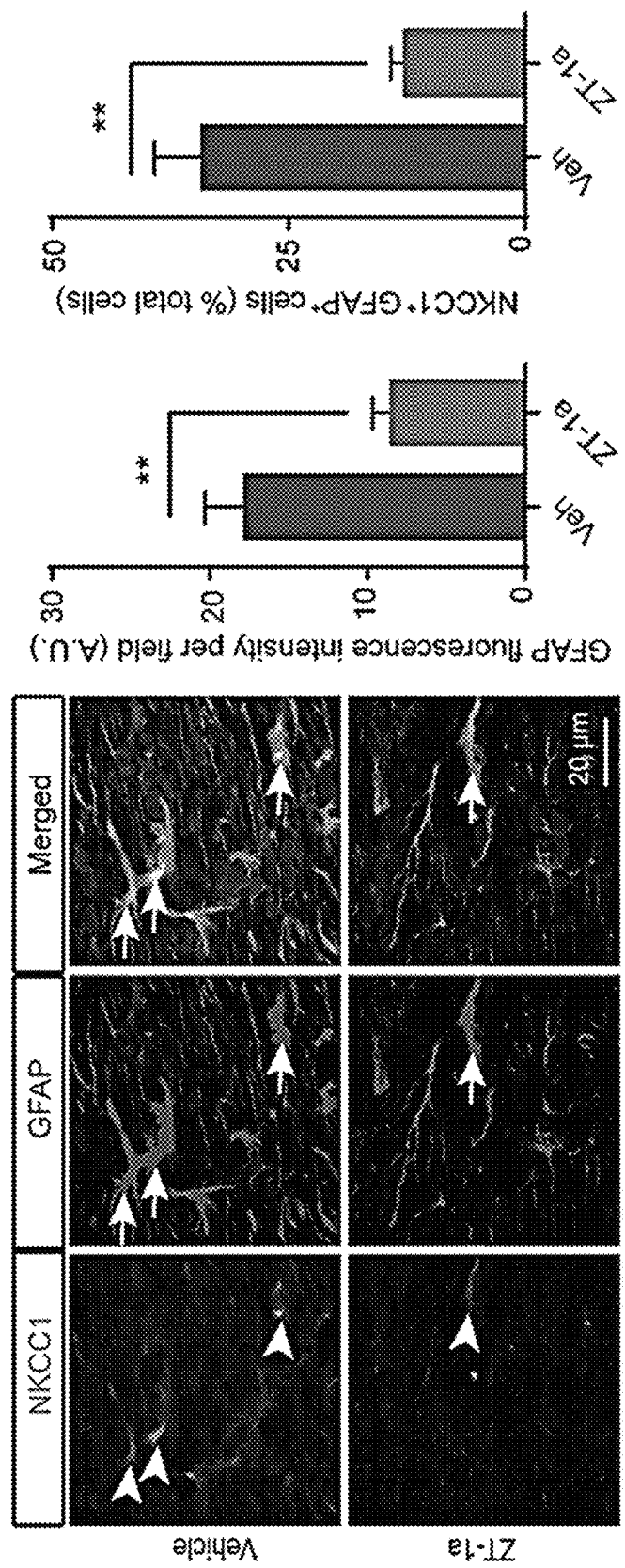
FIG. 6 shows representative data illustrating that ZT-1a attenuates NKCC1 and GFAP expressions in astrocytes in CC at 4 weeks after BCAS.

6. ZT-1a Attenuates BCAS-Induced Upregulation of GFAP and NKCC1 Proteins in GFAP$^+$ Reactive Astrocytes Without wishing to be bound by theory, it is speculated that ZT-1a treatment preserves white matter integrity via reducing reactive astrocyte-mediated inflammation in white matter tracks. FIG. 6 shows a concurrent decrease in GFAP expression (by ~50%) and in tNKCC1 expression (by ~60%) in CC of ZT-1a-treated mice. These results illustrate a close correlation between reduction of GFAP and tNKCC1 in the ZT-1a-treated brains. Data are mean±SEM, n=4, **p<0.01.

Figure 7A:
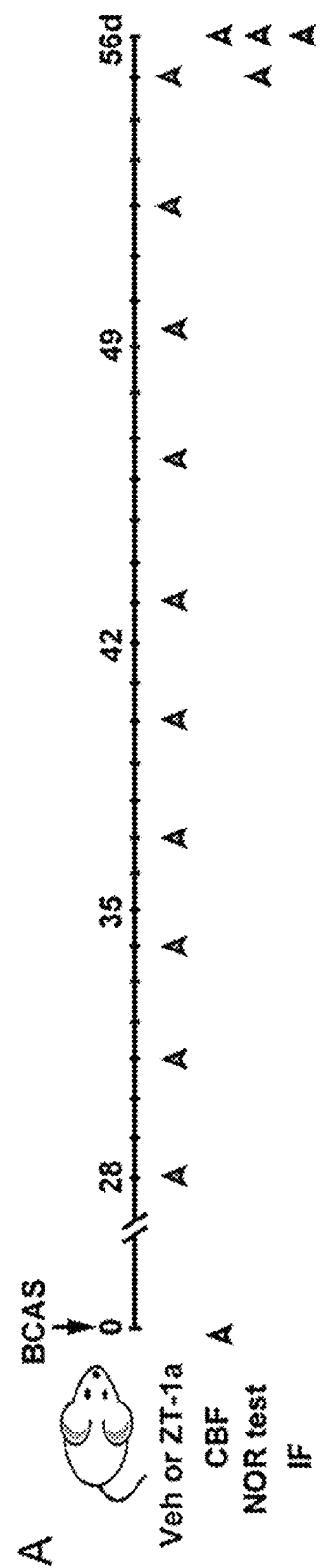
FIG. 7A-D show representative data illustrating that delayed SPAK inhibition improves memory deficits, myelination, and cerebral blood flow (CBF) after BCAS.
Figure 7B:
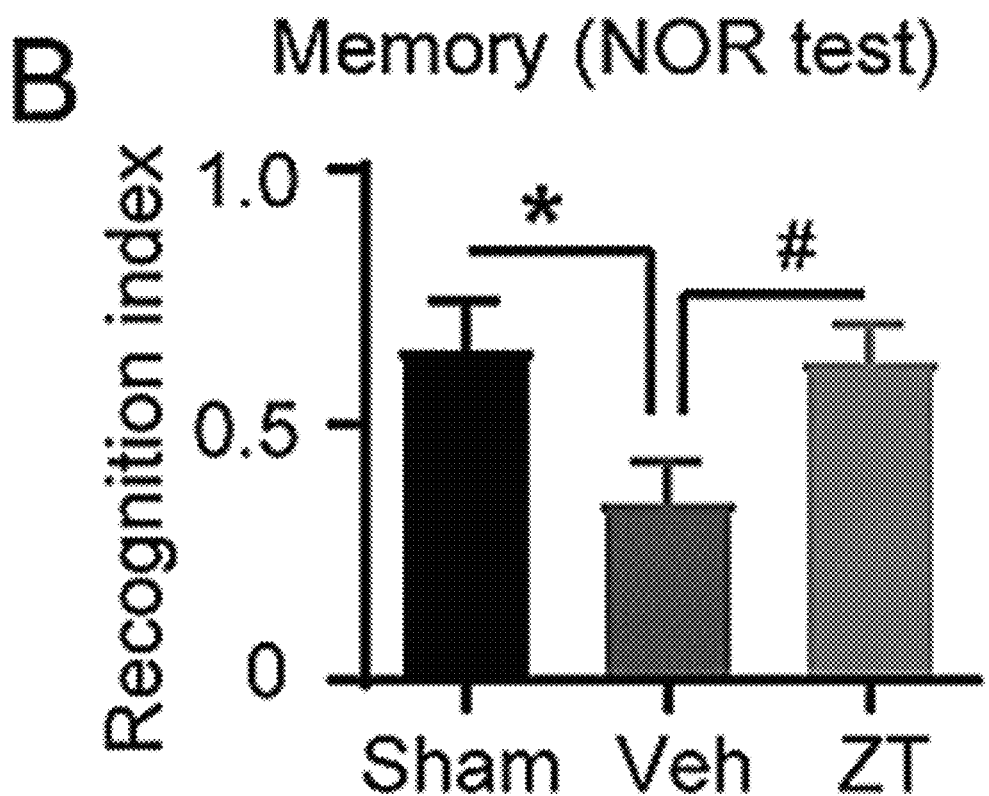
Figure 7C:
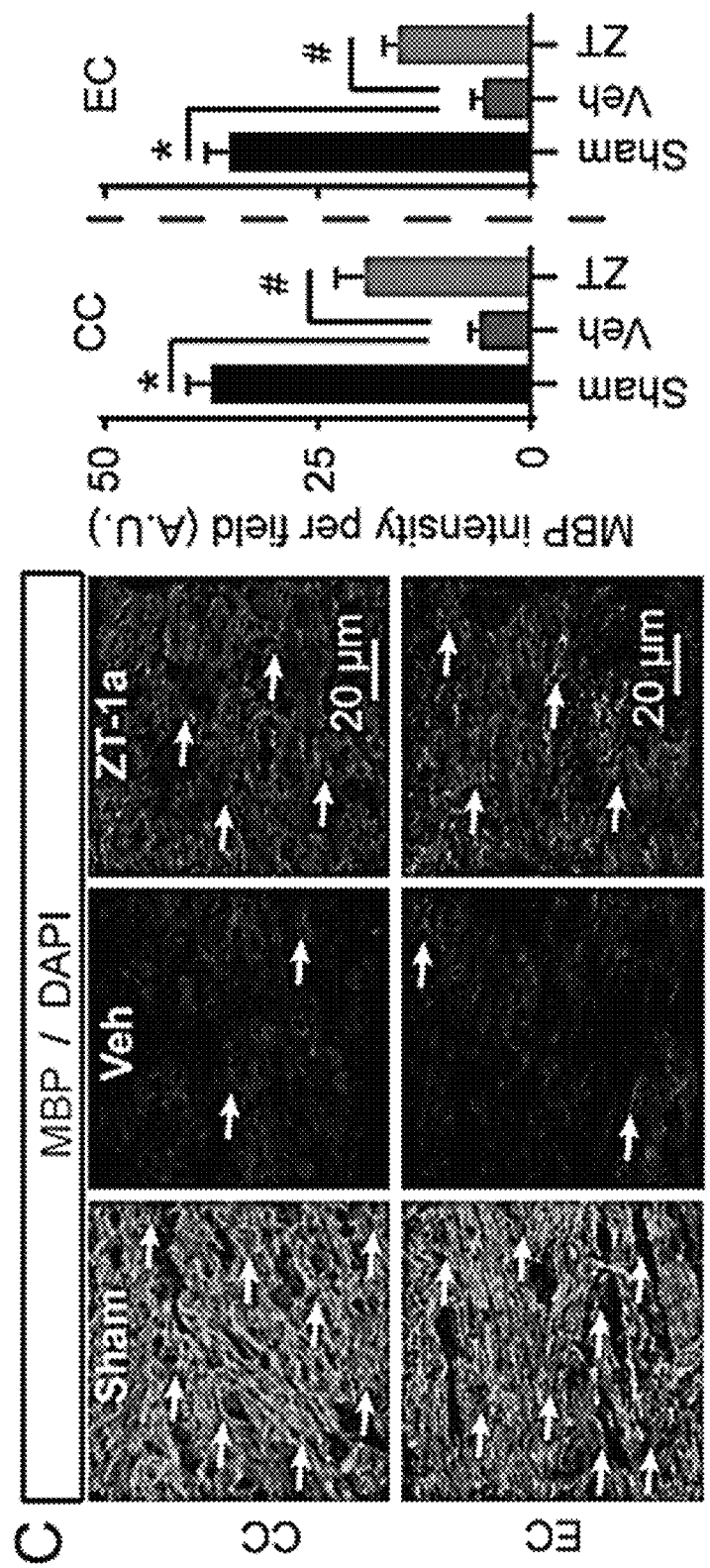
Figure 7D:
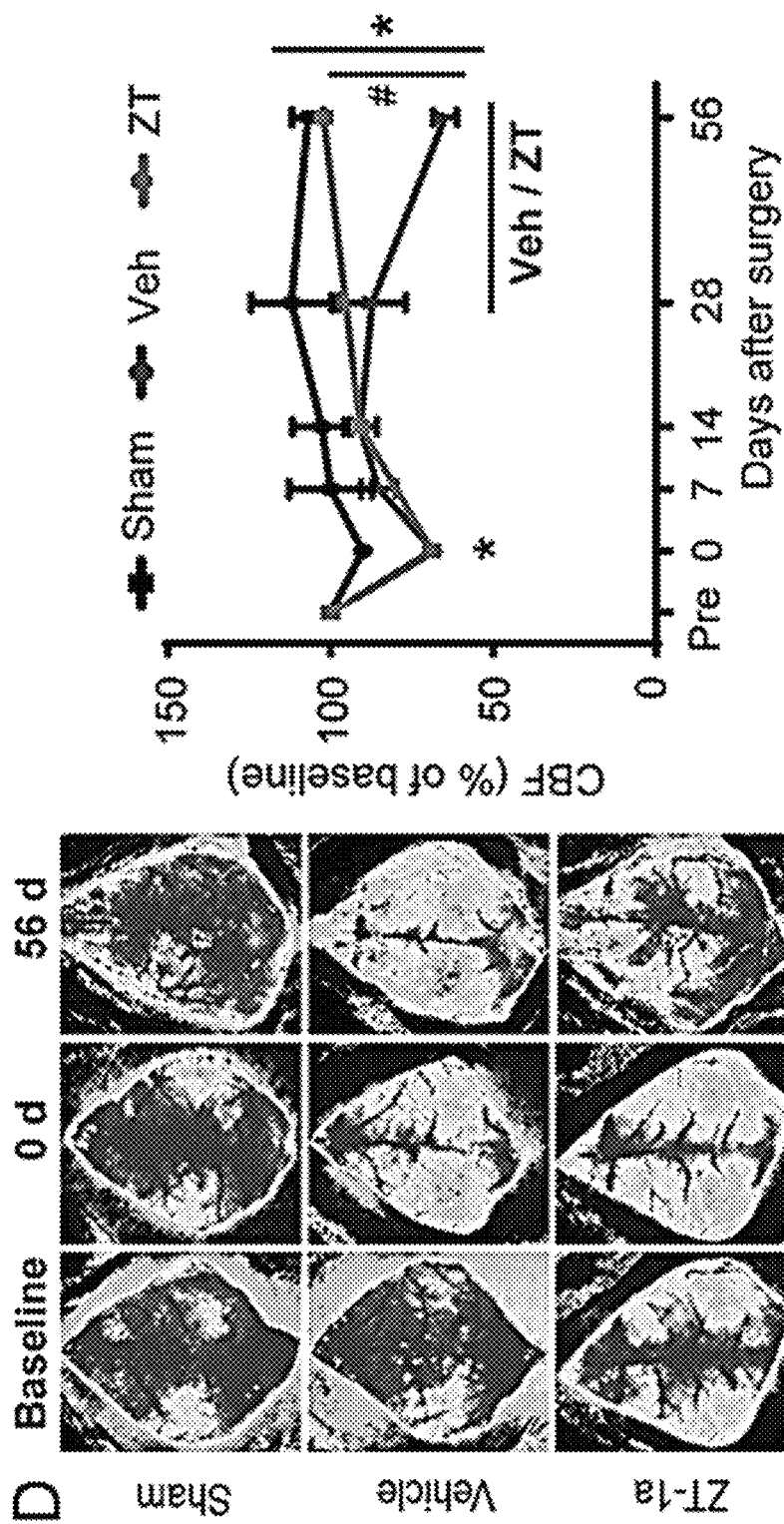

7. Delayed Administration of ZT-1a (4-8 wks Post-BCAS) is Equally Effective in Improving Memory Deficits, Myelination, as Well as Cerebral Blood Flow The efficacy of administration of ZT-1a starting at 4 wks post-BCAS surgery, when matter demyelination has reached its peak, was examined next. To test the reproducibility of these findings, in this pilot study, the Coil BCAS model was used by placing two microcoils (0.18 mm diameter) in each CCAs, a well-established model with CBF reduction and accompanied by ischemic lesion to white matter tracks, cortex, and hippocampus. Either vehicle DMSO (Veh, 2 ml/kg) or ZT-1a (5 mg/kg, every 72 h, i.p) was administered at 4-8 wks post-BCAS (i.e., during 28-56 days after coil-BCAS, every 3 days) (FIG. 7A). No body weight changes were detected in Sham, Veh, and ZT-1a-treated mice (data not shown). As shown in FIG. 7B, compared to Sham controls, the Veh-treated BCAS mice displayed memory deficits in the novel objective recognition test (NOR). In contrast, ZT-1a-treated BCAS mice exhibited no memory function impairment (FIG. 7B). Then MBP expression levels were examined in these brains by immunostaining. FIG. 7C shows massive loss of MBP protein expression in the CC and EC tracts of the Veh-treated BCAS brains. In contrast, the ZT-1a-treated brains exhibited significantly increased MBP levels (p<0.05, FIG. 7C), implying that delayed ZT-1a administration is effective in stimulating white matter remyelination, possibly, via increased oligodendrogenesis and maturation. In addition, it was also observed that delayed ZT-1a treatment for four weeks significantly improved CBF by 8 wks post-BCAS (FIG. 7D). Without wishing to be bound by theory, these new findings suggest that ZT-1a treatment may also restore peri-vascular astrocyte function, blood-brain-barrier integrity, and/or cerebral angiogenesis. Data are mean±SEM, n=5-8, *p<0.01 vs. sham, *p<0.05 vs. Veh.

8. Cellular Activity Profile of Inhibitors with the Salicyclic Amide

A list of the compounds evaluated for their ability to inhibit phosphorylation of SPAK/NKCC1/KCC3 activity is illustrated in Table 1 below.

TABLE 1

| No. | Structure | SPAK pSer373 (μM) Iso, hypo | NKCC1 pThr203 (μM) Iso, hypo | KCC3 pThr991 (μM) Iso, hypo | KCC3 pThr1048 (μM) Iso, hypo |
|---|---|---|---|---|---|
| 1a (ZT-1a) | 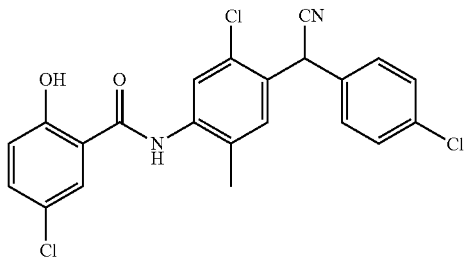 | 1, 3 | 1, 1 | 3, 3 | 1, 3 |
| 1b | 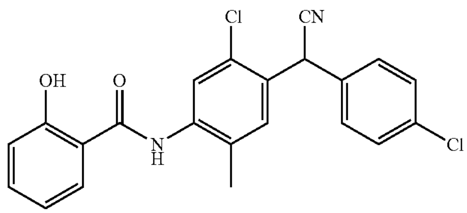 [SMILES: Cc1cc(C(C#N)c2ccc(Cl)cc2)c(Cl)cc1NC(=O)c1ccccc1O] | 3, 3 | 3, 1 | 10, 10 | 3, 3 |
| 1c (ZT-05-037-01) | 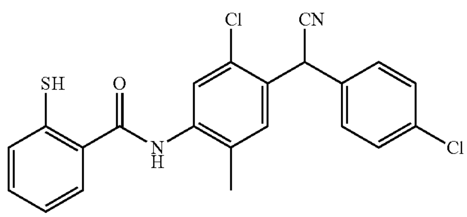 [SMILES: Cc1cc(C(C#N)c2ccc(Cl)cc2)c(Cl)cc1NC(=O)c1ccccc1S] | 3, 3 | 1, 3 | 10, 10 | 3, 3 |
| 1d (ZT-06-022-01) | 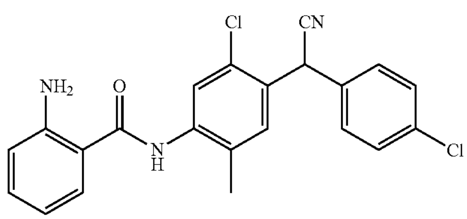 [SMILES: Cc1cc(C(C#N)c2ccc(Cl)cc2)c(Cl)cc1NC(=O)c1ccccc1N] | 3, 3 | 1, 3 | 10, 10 | 3, 3 |
| 1e | 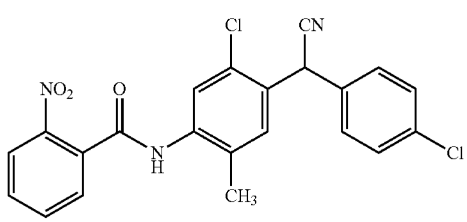 [SMILES: Cc1cc(C(C#N)c2ccc(Cl)cc2)c(Cl)cc1NC(=O)c1ccccc1[N+](=O)[O-]] | — | — | — | — |
| 1f | 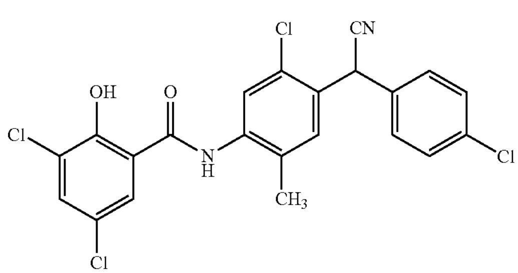 [SMILES: Cc1cc(C(C#N)c2ccc(Cl)cc2)c(Cl)cc1NC(=O)c1cc(Cl)cc(Cl)c1O] | 3, 3 | 1, 3 | 10, 10 | 3, 3 |

TABLE 1-continued

| No. | Structure | SPAK pSer373 (μM) Iso, hypo | NKCC1 pThr203 (μM) Iso, hypo | KCC3 pThr991 (μM) Iso, hypo | KCC3 pThr1048 (μM) Iso, hypo |
|---|---|---|---|---|---|
| 1g(ZT-06-055-01) | 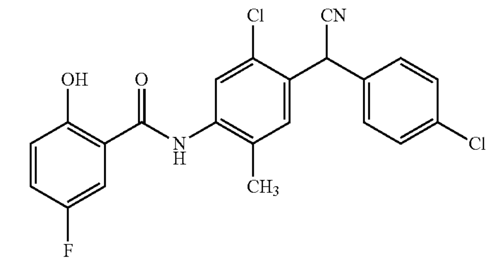 [SMILES: Cc1cc(C(C#N)c2ccc(Cl)cc2)c(Cl)cc1NC(=O)c1cc(F)ccc1O] | 3, 3 | 1, 3 | 10, 10 | 3, 3 |
| 1h(ZT-06-039-01) | 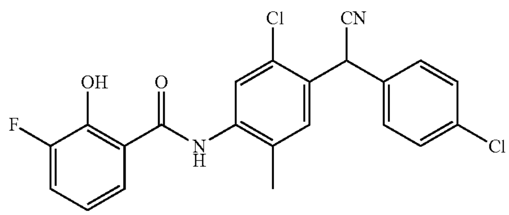 [SMILES: Cc1cc(C(C#N)c2ccc(Cl)cc2)c(Cl)cc1NC(=O)c1cccc(F)c1O] | 3, 3 | 1, 3 | 10, 10 | 3, 3 |
| 1i | 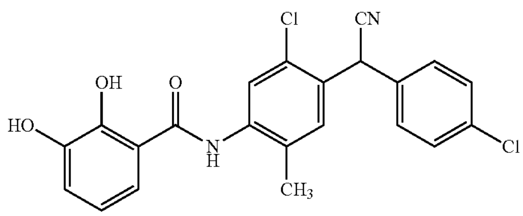 [SMILES: Cc1cc(C(C#N)c2ccc(Cl)cc2)c(Cl)cc1NC(=O)c1cccc(O)c1O] | — | — | — | — |
| 1j | 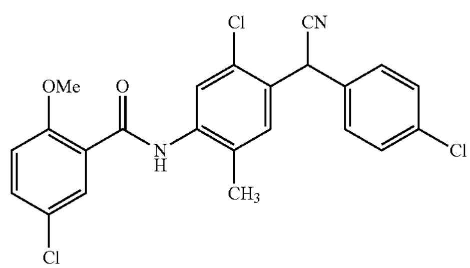 [SMILES: COc1ccc(Cl)cc1C(=O)Nc1cc(Cl)c(C(C#N)c2ccc(Cl)cc2)cc1C] | — | — | — | — |

"—" showed no inhibition of phosphorylation of SPAK/NKCC1/KCC3, values are means ± SEM that represent 50% inhibition of SPAK pSer373 under Isotonic or Hypotonic conditions, n = 3.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating and/or preventing a neurodegenerative disease or a neurocognitive disease in a subject in need thereof, the method comprising administering to the subject an effective amount of a compound having a structure represented by a formula:

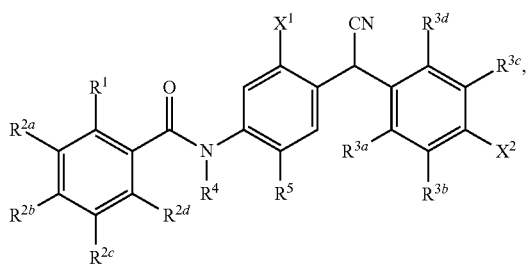

wherein each of $X^1$ and $X^2$ is independently halogen;

wherein $R^1$ is selected from —OH, —SR$^{10}$, and —NR$^{11a}$R$^{11b}$;

wherein each of $R^{10}$, $R^{11a}$, and $R^{11b}$, when present, is independently selected from hydrogen and C1-C4 alkyl;

wherein each of $R^{2a}$, $R^{2b}$, $R^{2c}$, and $R^{2d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino;

wherein each of $R^{3a}$, $R^{3b}$, $R^{3c}$, and $R^{3d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino;

wherein $R^4$ is selected from hydrogen and C1-C4 alkyl; and wherein $R^5$ is C1-C4 alkyl, provided that the compound is not:

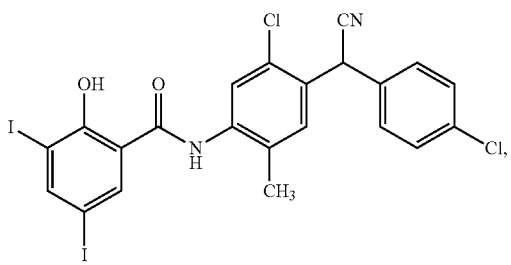 [SMILES: Cc1cc(C(C#N)c2ccc(Cl)cc2)c(Cl)cc1NC(=O)c1cc(I)cc(I)c1O]

or a pharmaceutically acceptable salt thereof, wherein the subject has not been diagnosed as having had an ischemic stroke prior to the administering step, and wherein the neurodegenerative disease is selected from Alzheimer's disease, cerebral autosomal dominant arteriopathy with sub-cortical infarcts and leukoencephalopathy (CADASIL), Parkinson's disease, Huntington's disease, amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia, and Lewy body disease.

2. The method of claim 1, wherein the compound has a structure represented by a formula:

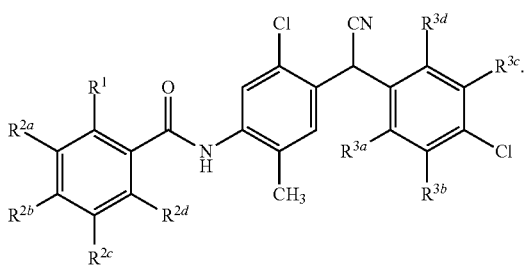

wherein $R^1$ is selected from —OH, —SR$^{10}$, and —NR$^{11a}$R$^{11b}$;

wherein each of $R^{10}$, $R^{11a}$, and $R^{11b}$, when present, is independently selected from hydrogen and C1-C4 alkyl;

wherein each of $R^{2a}$, $R^{2b}$, $R^{2c}$, and $R^{2d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino; and wherein each of $R^{3a}$, $R^{3b}$, $R^{3c}$, and $R^{3d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino.

3. The method of claim 1, wherein $R^1$ is —OH.

4. The method of claim 1, wherein $R^1$ is —SH.

5. The method of claim 1, wherein $R^1$ is —NH$_2$.

6. The method of claim 1, wherein each of $R^{2a}$, $R^{2b}$, $R^{2c}$, and $R^{2d}$ is independently selected from hydrogen, —F, —Cl, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino.

7. The method of claim 1, wherein each of $R^{2a}$, $R^{2b}$, $R^{2c}$, and $R^{2d}$ is hydrogen.

8. The method of claim 1, wherein at least one of $R^{2a}$, $R^{2b}$, $R^{2c}$, and $R^{2d}$ is halogen.

9. The method of claim 1, wherein each of $R^{2a}$, $R^{2b}$, $R^{2c}$, and $R_{2d}$ is independently selected from hydrogen, —F, and —Cl.

10. The method of claim 1, wherein the compound has a structure represented by a formula:

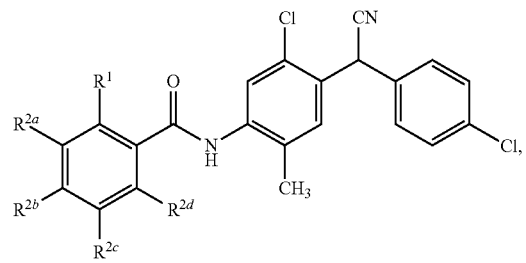

wherein $R^1$ is selected from —OH, —SR$^{10}$, and —NR$^{11a}$R$^{11b}$;

wherein each of $R^{10}$, $R^{11a}$, and $R^{11b}$, when present, is independently selected from hydrogen and C1-C4 alkyl; and wherein each of $R^{2a}$, $R^{2b}$, $R^{2c}$, and $R^{2d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino.

11. The method of claim 1, wherein the compound has a structure represented by a formula:

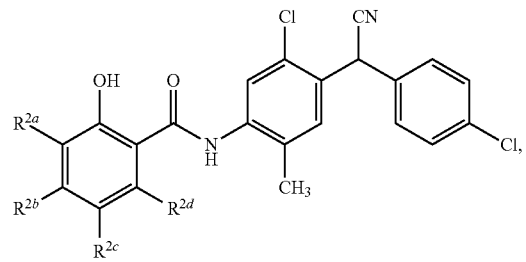

wherein each of $R^{2a}$, $R^{2b}$, $R^{2c}$, and $R^{2d}$ is independently selected from hydrogen, halogen, —NO$_2$, —CN, —OH, —SH, —NH$_2$, C1-C4 alkyl, C1-C4 haloalkyl, C1-C4 cyanoalkyl, C1-C4 hydroxyalkyl, C1-C4 alkoxy, C1-C4 thioalkyl, C1-C4 aminoalkyl, C1-C4 alkylamino, and (C1-C4)(C1-C4) dialkylamino.
12. The method of claim 1, wherein the compound is selected from:
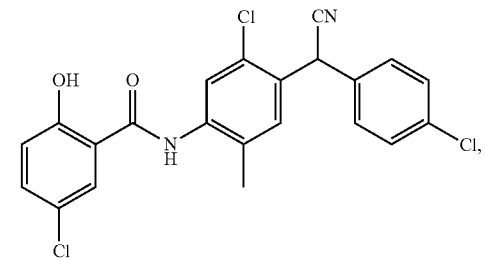 [SMILES: Cc1cc(C(C#N)c2ccc(Cl)cc2)c(Cl)cc1NC(=O)c1cc(Cl)ccc1O]
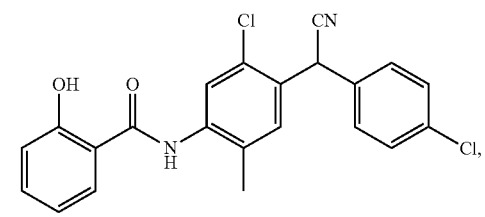
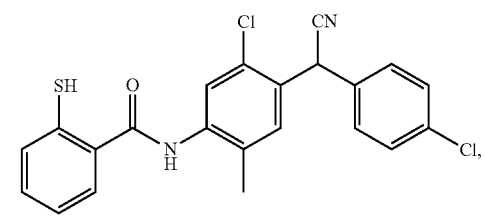
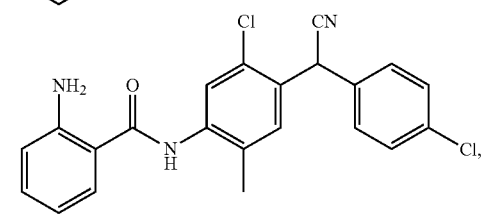
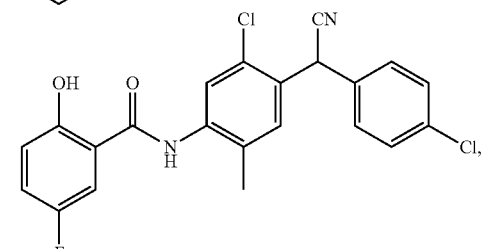
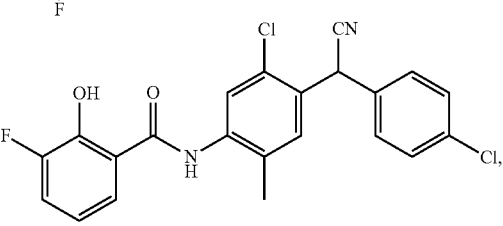
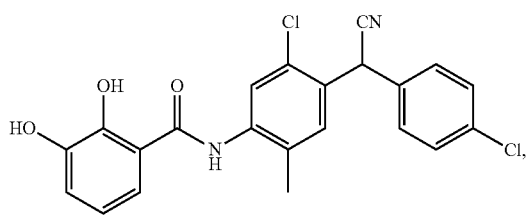
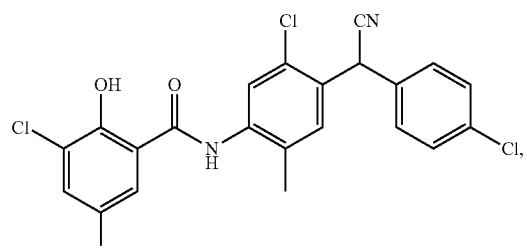
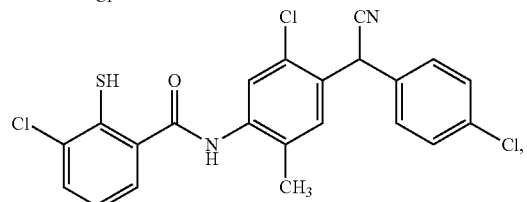
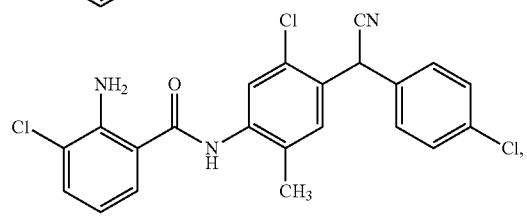
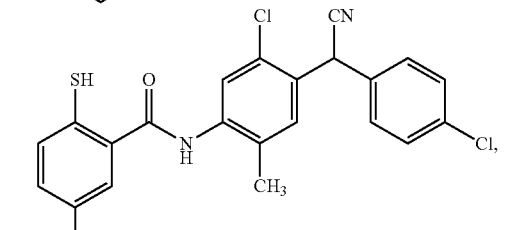
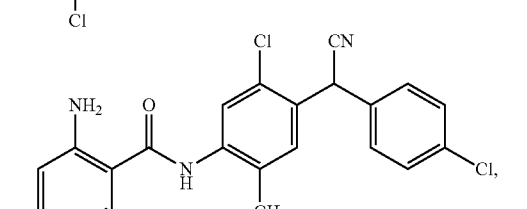
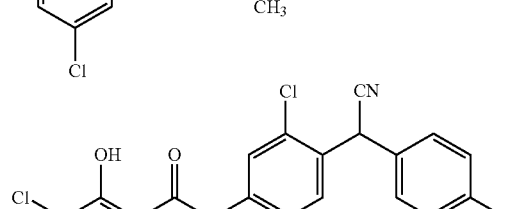
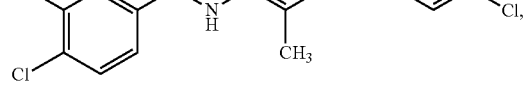

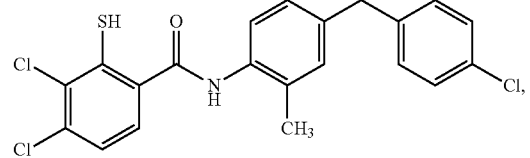
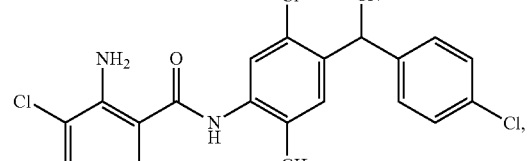
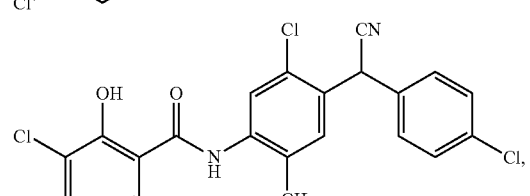
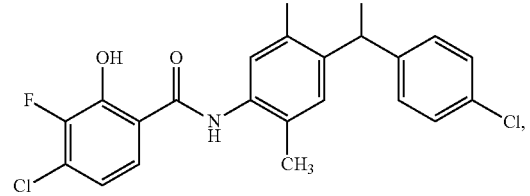
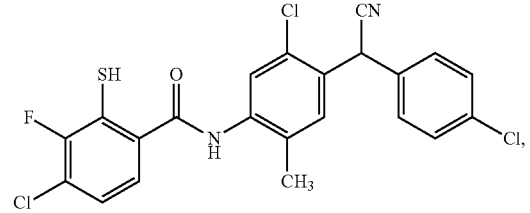
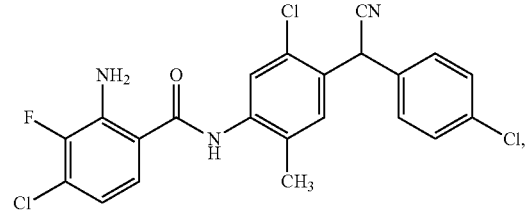
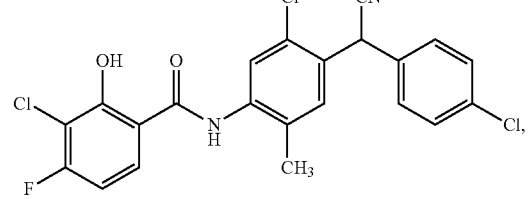
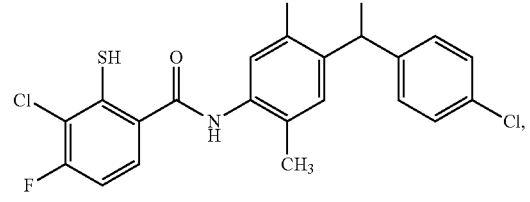
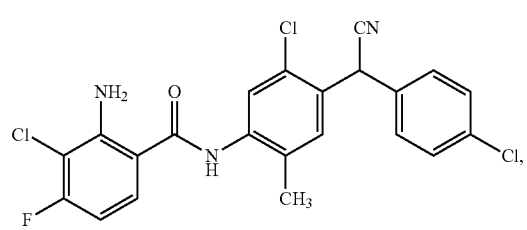
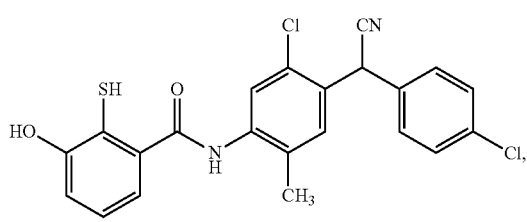
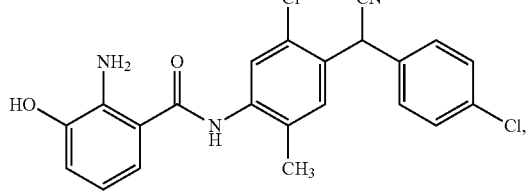
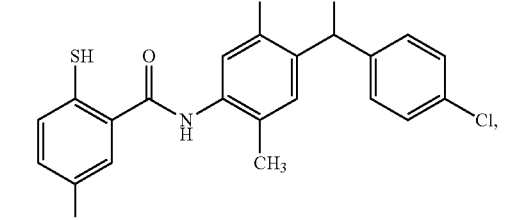
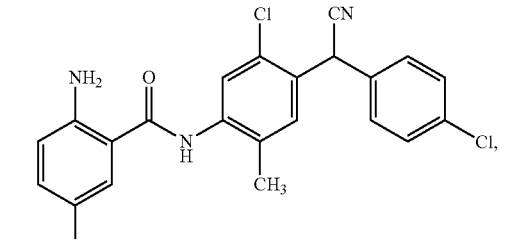
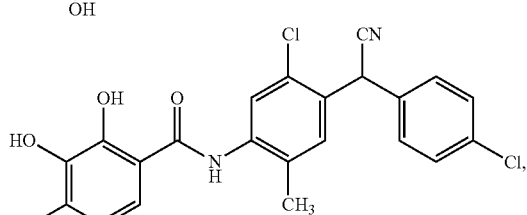
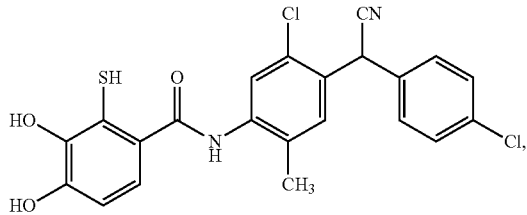

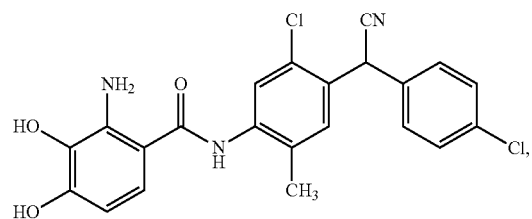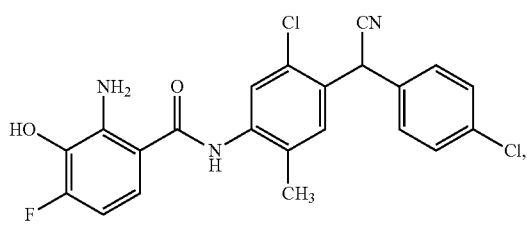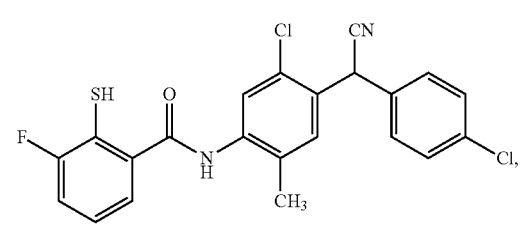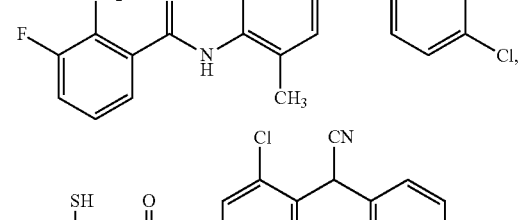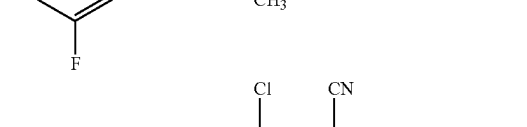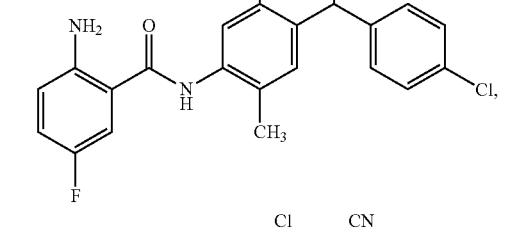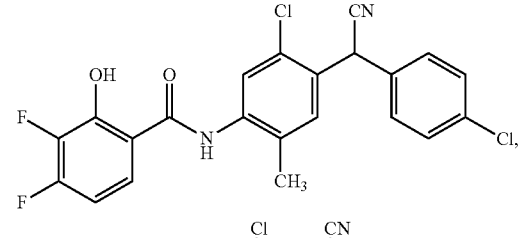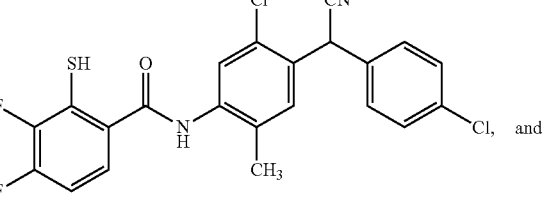

13. The method of claim 1, wherein the compound is:

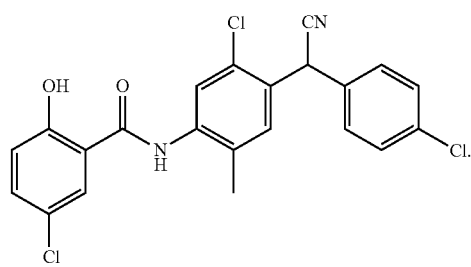 [SMILES: Cc1cc(C(C#N)c2ccc(Cl)cc2)c(Cl)cc1NC(=O)c1cc(Cl)ccc1O]

14. The method of claim 1, wherein the method does not comprise administering an inhibitor of COX-1, COX-2, or lipoxygenase to the subject.

15. The method of claim 1, wherein the method treats or prevents a neurocognitive disease, and wherein the neurocognitive disease is dementia.

16. The method of claim 15, wherein the dementia is vascular dementia, frontotemporal dementia, Lewy body dementia, or mixed dementia.

17. The method of claim 15, wherein the dementia is induced by Alzheimer's disease or Parkinson's disease.

18. A method of treating and/or preventing dementia in a subject in need thereof, the method comprising administering to the subject an effective amount of a compound having a structure represented by a formula:

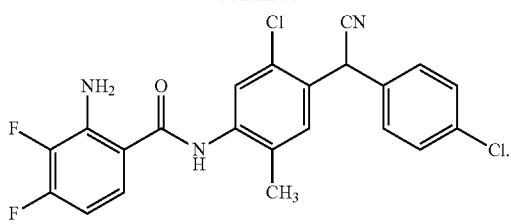

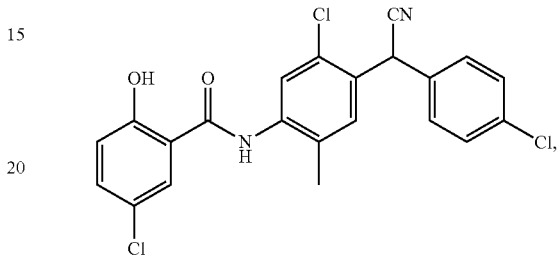

or a pharmaceutically acceptable salt thereof,
wherein the subject has not been diagnosed as having had an ischemic stroke prior to the administering step.

\* \* \* \* \*